US009187728B2

(12) United States Patent
Nishino et al.

(10) Patent No.: US 9,187,728 B2
(45) Date of Patent: Nov. 17, 2015

(54) METHOD FOR PRODUCING HEMATOPOIETIC STEM CELLS

(75) Inventors: Taito Nishino, Chiyoda-ku (JP); Atsushi Iwama, Chiba (JP)

(73) Assignees: Nissan Chemical Industries, Ltd., Tokyo (JP); NATIONAL UNIVERSITY CORPORATION CHIBA UNIVERSITY, Chiba-shi (JP)

( * ) Notice: Subject to any disclaimer, the term of this patent is extended or adjusted under 35 U.S.C. 154(b) by 200 days.

(21) Appl. No.: 13/704,424

(22) PCT Filed: Jun. 13, 2011

(86) PCT No.: PCT/JP2011/063537
§ 371 (c)(1),
(2), (4) Date: Dec. 14, 2012

(87) PCT Pub. No.: WO2011/158806
PCT Pub. Date: Dec. 22, 2011

(65) Prior Publication Data
US 2013/0095085 A1 Apr. 18, 2013

(30) Foreign Application Priority Data

Jun. 14, 2010 (JP) ................................. 2010-135431
Aug. 25, 2010 (JP) ................................. 2010-188594

(51) Int. Cl.
A61K 38/00 (2006.01)
C12N 5/00 (2006.01)
C12N 5/0789 (2010.01)
A61K 31/122 (2006.01)
A61K 31/352 (2006.01)

(52) U.S. Cl.
CPC ............ *C12N 5/0647* (2013.01); *A61K 31/122* (2013.01); *A61K 31/352* (2013.01); *C12N 2500/62* (2013.01); *C12N 2501/125* (2013.01); *C12N 2501/145* (2013.01); *C12N 2501/26* (2013.01); *C12N 2501/72* (2013.01); *C12N 2501/727* (2013.01); *C12N 2501/999* (2013.01)

(58) Field of Classification Search
None
See application file for complete search history.

(56) References Cited

U.S. PATENT DOCUMENTS

| 6,013,067 A | 1/2000 | Fibbe et al. | |
|---|---|---|---|
| 2006/0020027 A1* | 1/2006 | Balasubramanyam et al. | 514/517 |

FOREIGN PATENT DOCUMENTS

| JP | 10 510842 | 10/1998 |
|---|---|---|
| JP | 2000-23674 | 1/2000 |
| JP | 2000 72665 | 3/2000 |
| JP | 2000 351728 | 12/2000 |
| JP | 2000 355536 | 12/2000 |
| JP | 2001-161350 | 6/2001 |
| JP | 2002-502617 | 1/2002 |
| JP | 2009-40692 | 2/2009 |
| WO | WO 2004/046312 A2 | 6/2004 |
| WO | WO 2004/046312 A3 | 6/2004 |
| WO | WO 2010/065679 A1 | 6/2010 |

OTHER PUBLICATIONS

Extended Search Report issued Oct. 4, 2013 in European Application No. 11795711.8.
Subhash Padhye, et al., "Emerging role of Garcinol, the antioxidant chalcone from *Garcinia indica* Choisy and its synthetic analogs", Journal of Hematology & Oncology, vol. 2, No. 1, Sep. 2, 2009, pp. 1-13.
Taito Nishino, et al., "Ex Vivo Expansion of Human Hematopoietic Stem Cells by Garcinol, a Potent Inhibitor of Histone Acetyltransferase", PLOS One, vol. 6, No. 9, Sep. 12, 2011, pp. 1-9.
Li Lu, et al., "The Selective Enhancing Influence of Hemin and Products of Human Erythrocytes on Colony Formation by Human Multipotential ($CFU_{gemm}$) and Erythroid ($BFU_e$) Progenitor Cells in Vitro", International Society for Experimental Hematology, vol. 11, No. 8, Sep. 1983, pp. 721-729.
Akihiko Taguchi, et al., "Administration of $CD34^+$ cells after stroke enhances neurogenesis via angiogenesis in a mouse model", The Journal of Clinical Investigation, vol. 114, No. 3, Aug. 2004, pp. 330-338.
Donald Orlic, et al., "Bone marrow cells regenerate infarcted myocardium", Letters to Nature, vol. 410, Apr. 2001, pp. 701-705.
Erico Tateishi-Yuyama, et al., "Therapeutic angiogenesis for patients with limb ischaemia by autologous transplantation of bone-marrow cells: a pilot study and a randomised controlled trial", The Lancet, vol. 360, Aug. 10, 2002, pp. 427-435.
Philippe Menasche, "You Can't Judge a Book by Its Cover", Circulation, vol. 113, 2006, pp. 1275-1277.

(Continued)

*Primary Examiner* — Michail Belyavskyi
(74) *Attorney, Agent, or Firm* — Oblon, McClelland, Maier & Neustadt, L.L.P.

(57) ABSTRACT

An expanding agent for hematopoietic stem cells and/or hematopoietic progenitor cells useful as a therapy for various hematopoietic diseases and useful for improvement in the efficiency of gene transfer into hematopoietic stem cells for gene therapy is provided.
A method of producing hematopoietic stem cells and/or hematopoietic progenitor cells, which comprises expanding hematopoietic stem cells by culturing hematopoietic stem cells ex vivo in the presence of a compound represented by the formula following (I), a tautomer or pharmaceutically acceptable salt of the compound or a solvate thereof (wherein $R^1$ to $R^6$ are as defined in the description).

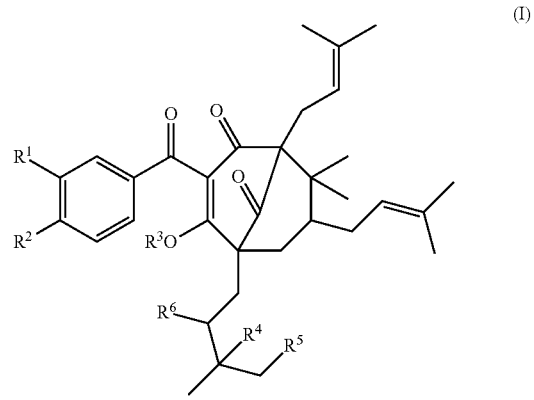

17 Claims, 3 Drawing Sheets

(56) References Cited

OTHER PUBLICATIONS

Joanne Kurtzberg, et al., "Placental Blood As a Source of Hematopoietic Stem Cells for Transplantation Into Unrelated Recipients", The New England Journal of Medicine, vol. 335, No. 3, Jul. 18, 1996, pp. 157-166.

Amit C. Nathwani, et al., "A review of gene therapy for haematological disorders", British Journal of Haematology, vol. 128, 2004, pp. 3-17.

Colleen Delaney, et al., "Notch-mediated Expansion of Human Cord Blood Progenitor Cells Capable of Rapid Myeloid Reconstitution", National Institutes of Health, Nat. Med., vol. 16, No. 2, Feb. 2010, 16 pages.

Hideo Ema, et al., "Colony Formation of Clone-Sorted Human Hematopoietic Progenitors", Blood, vol. 75, No. 10, May 15, 1990, pp. 1941-1946.

Lori Ishizawa, et al., "Immunomagnetic Separation of $CD34^+$ Cells From Human Bone Marrow, Cord Blood, and Mobilized Peripheral Blood", Journal of Hematotherapy, vol. 2, 1993, pp. 333-338.

Aliza Cassel, et al., "Retroviral-mediated gene transfer into CD34-enriched human peripheral blood stem cells", International Society for Experimental Hematology, vol. 21, 1993, pp. 585-591.

Mickie Bhatia, et al., "Purification of primitive human hematopoietic cells capable of repopulating immune-deficient mice", Medical Sciences, Proc. Natl. Acad. Sci. USA, vol. 94, May 1997, pp. 5320-5325.

André Larochelle, et al., "Identification of primitive human hematopoietic cells capable of repopulating NOD/SCID mouse bone marrow: Implications for gene therapy", Nature Medicine, vol. 2, No. 12, Dec. 1996, pp. 1329-1337.

Ami J. Shah, et al., "Flt3 Ligand Induces Proliferation of Quiescent Human Bone Marrow $CD34^+CD38^-$ Cells and Maintains Progenitor Cells in Vitro", Blood, vol. 87, No. 9, May 1, 1996, pp. 3563-3570.

John E. Dick, et al., "Assay of Human Stem Cells by Repopulation of NOD/SCID Mice", Hematopoietic Stem Cells; Stem Cells, vol. 15 (Suppl 1), 1997, pp. 199-207.

Takahiro Suzuki, et al., "Highly Efficient Ex Vivo Expansion of Human Hematopoietic Stem Cells Using Delta1-Fc Chimeric Protein", Stem Cells, vol. 24, 2006, pp. 2456-2465.

Ian McNiece, et al., "Ex vivo expanded peripheral blood progenitor cells provide rapid neutrophil recovery after high-dose chemotherapy in patients with breast cancer", Blood, vol. 96, No. 9, Nov. 1, 2000, pp. 3001-3007.

Kenneth Kaushansky, "Thrombopoietin and the Hematopoietic Stem Cell", Annals New York Academy of Sciences, vol. 1044, 2005, pp. 139-141.

Yutaka Kawano, et al., "Ex vivo expansion of G-CSF-mobilized peripheral blood $CD133^+$ progenitor cells on coculture with human stromal cells", Experimental Hematology, vol. 34, 2006, pp. 150-158.

Hiroshi Kawada, et al., "Rapid ex vivo expansion of human umbilical cord hematopoietic progenitors using a novel culture system", Experimental Hematology, vol. 27, 1999, pp. 904-915.

John P. Chute, et al., "Inhibition of aldehyde dehydrogenase and retinoid signaling induces the expansion of human hematopoietic stem cells", PNAS, vol. 103, No. 31, Aug. 1, 2006, pp. 11707-11712.

Mohammed Milhem, et al., "Modification of hematopoietic stem cell fate by 5aza 2' deoxycytidine and trichostatin A", Blood, vol. 103, No. 11, Jun. 1, 2004, pp. 4102-4110.

Anskar Y.H. Leung, et al., "All-trans retinoic acid (ATRA) enhances maintenance of primitive human hematopoietic progenitors and skews them towards myeloid differentiation in a stroma-noncontact culture system", Experimental Hematology, vol. 33, 2005, pp. 422-427.

Frederick R. Appelbaum, "The Use of Colony Stimulating Factors in Marrow Transplantation", Cancer Supplement, vol. 72, No. 11, Dec. 1, 1993, pp. 3387-3392.

Nishino, T. et al., "OS-1-180 Ex vivo expansion of hematopoletic stem and progenitor cells using a natural product, Garcinol," The Japanese Journal of Clinical Hematology, vol. 51, No. 9, p. 964, (Sep. 2010).

Ahmad, A. et al., "Apoptosis-Inducing Effect of Garcinol Is Mediated by NF- kB Signaling in Breast Cancer Cells," Journal of Cellular Biochemistry, vol. 109, No. 6, pp. 1134 to 1141, (Apr. 2010).

Matsumoto, K. et al., "Cytotoxic Benzophenone Derivatives from Garcinia Species Display a Strong Apoptosis-Inducing Effect against Human Leukemia Cell Lines," Biol. Pharm. Bull. vol. 26, No. 4, pp. 569 to 571, (2003).

International Search Report Issued Aug. 16, 2011 in PCT/JP11/63537 Filed Jun. 13, 2011.

* cited by examiner

METHOD FOR PRODUCING HEMATOPOIETIC STEM CELLS

TECHNICAL FIELD

The present invention relates to a method of expanding hematopoietic stem cells and/or hematopoietic progenitor cells using a compound having a blood cell expanding effect, in particular, to a method of expanding hematopoietic stem cells and/or hematopoietic progenitor cells by culturing hematopoietic stem cells in a culture medium containing at least one species selected from various cytokines and growth factors, a gene therapy method using the expanding method, a cell therapy material using hematopoietic stem cells and/or hematopoietic progenitor cells obtained by the expanding method and an expanding agent for hematopoietic stem cells, which contains the compound as an active ingredient and is useful for treatment of anemia or the like.

BACKGROUND ART

Blood contains various lineages of blood cells having biological functions, such as the erythrocytic lineage associated with oxygen delivery, the megakaryocytic lineage generating thrombocytes, the granulocytic lineage associated with prevention of infections, the myeloid lineage such as monocytes and/or macrophages and the lymphocytic lineage responsible for immunity such as T cells and B cells. All these blood cells differentiate and mature from the common origin, hematopoietic stem cells, and are maintained and generated in an individual throughout its life. Hematopoietic stem cells are defined as cells having both pluripotency which allows them to differentiate into functional cells such as lymphocytes, erythrocytes and leukocytes and the ability to regenerate themselves while maintaining the pluripotency (self-renewal).

Previous studies have revealed that hematopoietic stem cells first diverge two ways into the myeloid lineage and the lymphoid lineage, then differentiate into myeloid stem cells (mixed colony forming cells, CFU-GEMM) and into lymphoid stem cells, respectively. Further, myeloid stem cells differentiate into erythrocytes via erythroid burst forming cells (BFU-E) and erythroid colony forming cells (CFU-E), into thrombocytes via megakaryocyte colony forming cells (CFU-MEG), into monocytes, neutrophils and basophils via granulocyte-macrophage colony forming cells (CFU-GM), and into eosinophils via eosinophil colony forming cells (CFU-EO), while lymphoid stem cells differentiate into T cells via T lymphoid progenitor cells and into B cells via B lymphoid progenitor cells. Among them, cells forming multipotential colonies with diameters of at least 1 mm are called HPP-CFU colony forming cells and are known as the least differentiated hematopoietic progenitor cells, along with mixed colony forming cells (CFU-GEMM). These myeloid stem cells and various hematopoietic progenitor cells derived from them are identified by the properties of colonies they form on soft agar, semisolid methylcellulose media or the like in the presence of various cytokines (Non-Patent Document 1).

In recent years, as a curative therapy for a number of intractable diseases such as various blood diseases attributed to hematopoietic dysfunction and immune dysfunction, cancer, immunodeficiency, autoimmune diseases and inborn error of metabolism, autologous or allogeneic transplantation of hematopoietic stem cells have been performed. Quite recently, the effectiveness of transplantation of $CD34^+$ cells including hematopoietic stem cells in treating cerebral infarction, myocardial infarction and obstructive arteriosclerosis was reported (Non-Patent Documents 2, 3, 4 and 5). Attempts to regenerate nerves and muscles through hematopoietic stem cell transplantation are in progress. For example, nerve regeneration in cerebral infarction model mice through angiogenesis caused by transplantation of cord blood-derived $CD34^+$ cells (Non-Patent Document 2) and the possibility of repair of damaged muscles using $CD34^+$ cells were reported (Non-Patent Document 5 and Patent Document 1). Among them, bone marrow transplantation has been used in many cases of treatment and most established as a standard hematopoietic cell transplantation therapy. However, because for bone marrow transplantation, the human leukocyte antigens (HLA) of the bone marrow donor and the transplant recipient have to match closely, there is a problem that bone marrow from donors are in short supply. Besides, the need for at least 4 days of hospitalization and pain, fever and bleeding caused by collection of a large amount of bone marrow are a heavy burden to donors.

In addition to bone marrow, peripheral blood is also used as an alternative source of hematopoietic stem cells nowadays. Hematopoietic stem cells mobilized from the bone marrow to peripheral blood by administration of granulocyte colony stimulating factor (G-CSF) to a human are used for transplantation after enrichment using a blood cell separator. However, donors for peripheral blood hematopoietic stem cell transplantation have to bear a heavy burden of the need for administration of G-CSF for 4 to 6 consecutive days which may cause side effects (such as blood coagulation and spleen hypertrophy). Besides, because the efficiency of the mobilization of hematopoietic stem cells from the bone marrow to peripheral blood by G-CSF varies from donor to donor, hematopoietic stem cells are not obtained sufficiently in some cases.

Just recently, it has been found that cord blood contains the same degree of hematopoietic stem cells as bone marrow and is useful for hematopoietic stem cell transplantation (Non-Patent Document 6). Because cord blood transplantation does not require complete HLA matching and is less likely to cause severe acute graft-versus-host disease (GVHD) than bone marrow and peripheral blood transplantation, cord blood is established as useful and has been used more frequently. However, because cord blood is obtained in a small amount from one donor and does not contain many hematopoietic stem cells, its use is mainly limited to children.

Furthermore, hematopoietic stem cells are also considered as useful cells for gene therapy of fatal genetic diseases with no effective cure, HIV infection, chronic granulomatosis and germ cell tumor. However, in order to transfect hematopoietic stem cells with a retrovirus vector carrying a target gene efficiently, it is necessary to artificially promote the proliferation of hematopoietic stem cells, which are usually in the stationary phase, by recruiting them into the cell cycle. Besides, in order to be successfully transplanted and express a transgene for a long time, the transfected hematopoietic stem cells have to be kept undifferentiated in culture ex vivo. Therefore, gene transfer by an improved cell culture method has been desired for efficient gene transfer and successful transplantation therapy (Non-Patent Document 7).

Meanwhile, hematopoietic progenitor cells are important for initial hematopoietic recovery after bone marrow or cord blood transplantation and are considered as effective, especially, in preventing early posttransplant infections. Therefore, transplantation of an insufficient number of hematopoietic progenitor cells can delay initial hematopoietic recovery and lower the posttransplant survival rate (Non-Patent Document 8).

To solve the above-mentioned problems with hematopoietic stem cell transplantation and gene therapy, a technique for expanding hematopoietic stem cells and/or hematopoietic progenitor cells ex vivo is demanded, and various culture methods have been attempted so far.

Here, hematopoietic stem cells and hematopoietic progenitor cells, which are to be cultured, are explained. It was revealed that in human, hematopoietic stem cells and various hematopoietic progenitor cells derived from them are found in populations of $CD34^+$ cells expressing the CD34 molecule as a cell surface antigen, and hence hematopoietic stem cells can be enriched as a $CD34^+$ cell population (Non-Patent Document 9). Specifically speaking, they are often enriched by mixing a cell population to be separated with a CD34 antibody labeled with magnetic beads and magnetically collecting $CD34^+$ cells (Non-Patent Documents 10 and 11). $CD34^+$ cell populations contain less than 10% of $CD34^+$ $CD38^-$ cell populations not expressing the CD38 molecule as a cell surface antigen. It has come to be considered that hematopoietic stem cells are more enriched in $CD34^+CD38^-$ cell populations than in $CD34^+$ cell populations (Non-Patent Documents 12 and 13). In order to determine the proportion of undifferentiated hematopoietic progenitor cells in a cell population, HPP-CFU colony forming cells are usually counted as mentioned above (Non-Patent Document 14). In recent years, it has become possible to experimentally test for the presence of human hematopoietic stem cells which have bone marrow repopulating ability by using NOD/SCID mice obtained by crossing diabetic mice and immunodeficient mice. The cells detected by this assay are called SCID-repopulating cells (SRC) and considered the closest to human hematopoietic stem cells (Non-Patent Document 15).

Conventional techniques for expanding hematopoietic stem cells and/or hematopoietic progenitor cells will also be explained. As mentioned above, since hematopoietic stem cells are more enriched in $CD34^+$ cells, $CD34^+$ cells are mainly used as the starting cells for expansion. Expansion of hematopoietic stem cells and hematopoietic progenitor cells from $CD34^+$ cells in culture in the presence of a cytokine or a growth factor such as stem cell factor (SCF), interleukin-3 (IL-3), interleukin-6 (IL-6), interleukin-6 (IL-6)/soluble IL-6 receptor complex, interleukin-11 (IL-11), granulocyte colony stimulating factor (G-CSF), granulocyte-macrophage colony stimulating factor (GM-CSF), flk2/flt3 ligand (FL), thrombopoietin (TPO) and erythropoietin or Notch ligand (such as Delta 1) has been reported (Patent Documents 2 and 3 and Non-Patent Documents 8, 14, 16 and 17). Among them, TPO has especially excellent effect on hematopoietic stem cell expansion and used for in most of cases of expansion (Non-Patent Document 18). Hematopoietic stem cells and hematopoietic progenitor cells expand in culture in the presence of such various cytokines and growth factors, but hematopoietic stem cells expand only by several times. Besides, these cytokines and growth factors are all produced as recombinant proteins, it may be difficult to obtain them for expansion stably, in a large amount, at low cost, or quickly.

For ex vivo expansion of hematopoietic stem cells, coculture systems using a different type of cells as feeder cells in the presence of various cytokines were reported. For example, expansion of hematopoietic stem cells in coculture with human bone marrow stromal cells was attempted (Non-Patent Document 19). An attempt to expand $CD34^+$ cells in the presence of TPO, FL and SCF using mouse bone marrow cell line HESS-5 was also reported (Non-Patent Document 20). However, because these coculture systems use foreign cells, there is a risk that cells infected with an unknown pathogen whose existence has not been confirmed may also be transplanted to patients. Furthermore, when stromal cells from a different kind of animal are used, the stromal cells have to be separated completely from $CD34^+$ cells because otherwise there is a risk of causing immune response in the recipient after transplantation.

In addition, ex vivo expansion of hematopoietic stem cells in culture in the presence of various cytokines such as TPO combined with low molecular weight compounds, not just various cytokines only, has been reported. Examples of such low molecular weight compounds include copper chelators, the combination of a histone deacetylase inhibitor and a DNA methylase inhibitor, all-trans retinoic acid, aldehyde dehydrogenase inhibitors (Non-Patent Documents 21, 22 and 23 and Patent Document 4). However, addition of any of them is not effective enough since hematopoietic stem cells expand by only several times, or cells have to be cultured for about 3 weeks.

It is known that treatments which promote rapid hematopoietic and immune recovery after transplantation of hematopoietic stem cells are quite effective in eliminating the risk of infections and shortening hospitalization. As such a treatment, posttransplant administration of the hematopoietic cytokine, granulocyte colony stimulating factor (G-CSF), is conducted in clinical settings (Non-Patent Document 24). However, it is effective only for leukocytes, and effective treatments which promote recovery of blood cells of all lineages through expansion of hematopoietic stem cells and/or hematopoietic progenitor cells are demanded. Effective therapies for diseases and dysfunctions accompanied by decrease in hematopoietic stem cells and/or hematopoietic progenitor cells, other than hematopietic stem cell transplantation, are also demanded.

PRIOR ART DOCUMENT

Patent Documents

Patent Document 1: JP-A-2009-40692
Patent Document 2: JP-A-2001-161350
Patent Document 3: JP-A-2000-23674
Patent Document 4: JP-A-2002-502617

Non-Patent Documents

Non-Patent Document 1: Lu, L. et al.; Exp. Hematol., 11, 721-9, 1983
Non-Patent Document 2: Taguchi, A et al.; J Clin Invest., 114, 330-8. 2004
Non-Patent Document 3: Orlic, D et al.; Nature, 410, 701-5. 2001
Non-Patent Document 4: Tateishi-Yuyama, E et al.; Lancet, 360, 427-35. 2002
Non-Patent Document 5: Iwasaki, H et al.; Circulation, 113, 1275-7. 2006
Non-Patent Document 6: Kurtzbert, J. et al.; New Eng. J. Med., 335, 157-66, 1996
Non-Patent Document 7: Nathwani, A C. et al.; Br J. Haematol., 128, 3-17, 2005
Non-Patent Document 8: Delaney, C. et al.; Nat. Med., 16, 232-6, 2010
Non-Patent Document 9: Ema, H. et al.; Blood, 75, 1941-6, 1990
Non-Patent Document 10: Ishizawa, L. et al.; J Hematother., 2, 333-8, 1993
Non-Patent Document 11: Cassel, A. et al.; Exp. Hematol., 21, 585-91, 1993

Non-Patent Document 12: Bhatia, M. et al.; Proc. Natl. Acad. Sci. USA 94:5320-25, 1997
Non-Patent Document 13: Larochelle, A. et al.; Nat. Med., 2, 1329-37, 1996
Non-Patent Document 14: Shah, A J et al.; Blood., 87, 3563-3570, 1996
Non-Patent Document 15: Dick, J E et al.; Stem Cells., 15, 199-203, 1997
Non-Patent Document 16: Suzuki, T et al.; Stem Cells., 24, 2456-2465, 2006
Non-Patent Document 17: McNiece et al., Blood.; 96, 3001-3007, 2000
Non-Patent Document 18: Kaushansky, K et al.; Ann NY Acad Sci., 1044,139-141, 2005
Non-Patent Document 19: Kawano, Y et al.; Exp Hematol., 34, 150-8, 2006
Non-Patent Document 20: Kawada, H et al.; Exp Hematol., 5, 904-15, 1999
Non-Patent Document 21: Chute, J P et al.; Proc Natl Acad Sci USA., 103, 11707-12, 2006
Non-Patent Document 22: Milhem, M et al.; Blood., 103, 4102-10, 2004
Non-Patent Document 23: Leung, A Y et al.; Exp Hematol., 33, 422-7, 2005
Non-Patent Document 24: Appelbaum, F R.; Cancer., 72, 3387-92. 1993

DISCLOSURE OF THE INVENTION

Technical Problem

An object of the present invention is to expand hematopoietic stem cells and/or hematopoietic progenitor cells ex vivo efficiently in a short term using a biologically safe and inexpensively obtainable compound. Another object of the present invention is to use an index more effective than conventional ones in determining the expansion effect of such a compound on hematopoietic stem cells. A still another object of the present invention is to provide an expansion agent for hematopoietic stem cells and/or hematopoietic progenitor cells useful for improvement in the efficiency of gene transfer into hematopoietic stem cells for gene therapy and useful for treatment of various hematopoietic disorders caused by dysfunctional hematopoietic stem cells and/or hematopoietic progenitor cells and muscle and nerve diseases accompanying damaged tissues. A still another object of the present invention is to provide a pharmaceutical agent effective for diseases which can be prevented, cured or alleviated through in vivo expansion of hematopoietic stem cells and/or hematopoietic progenitor cells.

Solution to Problems

The present inventors conducted extensive research on compounds having expansion activity to find a method of expanding hematopoietic stem cells and/or hematopoietic progenitor cells from human hematopoietic stem cells. As a result, the present inventors found that the compounds represented by the following formula show excellent expansion activity on $CD34^+$ cells, $CD34^+CD38^-$ cells, HPP-CFU colony forming cells, and SRC and are highly useful as an expansion agent for human hematopoietic stem cells and/or hematopoietic progenitor cells and accomplished the present invention.

Namely, the present invention relates to:
(1) A method of producing hematopoietic stem cells and/or hematopoietic progenitor cells, which comprises expanding hematopoietic stem cells and/or hematopoietic progenitor cells by culturing hematopoietic stem cells ex vivo in the presence of a compound represented by the following formula (I), a tautomer or pharmaceutically acceptable salt of the compound or a solvate thereof:

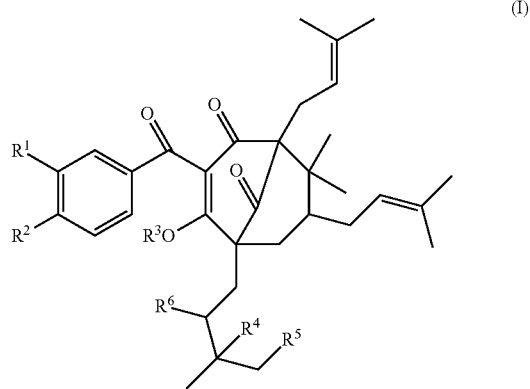

(I)

wherein each of $R^1$ and $R^2$ which may be identical or different is a hydrogen atom, a $C_{1-3}$ alkyl group, a $C_{1-3}$ alkoxy group, a hydroxyl group, a $C_{1-3}$ alkylsulfonyl group, a monosaccharide residue, an oligosaccharide residue or an amino acid residue,
$R^3$ is a hydrogen atom or forms a single bond, together with $R^4$, $R^4$ forms a single bond together with $R^3$ or forms a single bond together with $R^5$,
$R^5$ is a hydrogen atom or forms a single bond together with $R^4$, and $R^6$ is a $C_{1-10}$ alkyl group or a $C_{2-10}$ alkenyl group.
(2) The method of producing hematopoietic stem cells and/or hematopoietic progenitor cells according to (1), wherein $R^1$ and $R^2$ are hydroxyl groups.
(3) The method of producing hematopoietic stem cells and/or hematopoietic progenitor cells according to (1) or (2), wherein $R^6$ is a 3-methyl-2-butenyl group or a 3-methyl-3-buetnyl group.
(4) The method of producing hematopoietic stem cells and/or hematopoietic progenitor cells according to any one of (1) to (3), wherein $R^3$ is a hydrogen atom, and $R^4$ and $R^5$ forms a single bond together with each other.
(5) The method of producing hematopoietic stem cells and/or hematopoietic progenitor cells according to (4), wherein the compound represented by the formula (I) is the compound represented by the following formula (II).

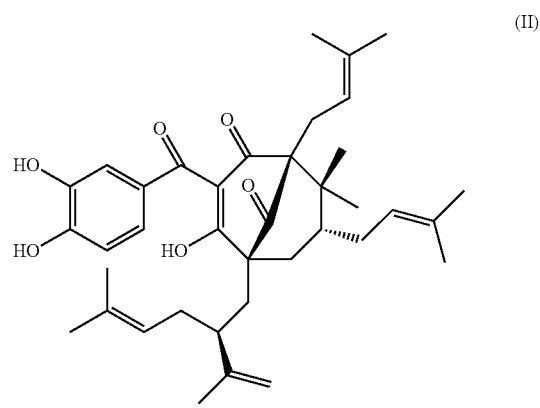

(II)

(6) The method of producing hematopoietic stem cells and/or hematopoietic progenitor cells according to any one of (1) to (3), wherein $R^3$ and $R^4$ forms a single bond together with each other, $R^5$ is a hydrogen atom, and $R^6$ is a 3-methyl-2-butenyl group.

(7) The method of producing hematopoietic stem cells and/or hematopoietic progenitor cells according to (6), wherein the compound represented by the formula (I) is the compound represented by the following formula (III).

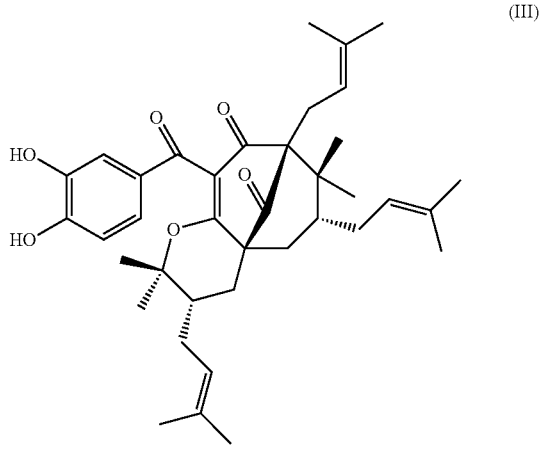

(8) The method of producing hematopoietic stem cells and/or hematopoietic progenitor cells according to any one of (1) to (7), wherein the hematopoietic stem cells and/or hematopoietic progenitor cells to be cultured ex vivo are CD34$^+$ cells.
(9) The method of producing hematopoietic stem cells and/or hematopoietic progenitor cells according to any one of (1) to (7), wherein the hematopoietic stem cells and/or hematopoietic progenitor cells to be cultured ex vivo are CD34$^+$CD38$^-$ cells.
(10) The method of producing hematopoietic stem cells and/or hematopoietic progenitor cells according to any one of (1) to (7), wherein the cells to be expanded are HPP-CFU colony forming cells.
(11) The method of producing hematopoietic stem cells and/or hematopoietic progenitor cells according to any one of (1) to (7), wherein the cells to be expanded are SCID-repopulating cells (SRC).
(12) The method of producing hematopoietic stem cells and/or hematopoietic progenitor cells according to any one of (1) to (11), which uses a culture medium containing at least one blood cell stimulating factor.
(13) The method of producing hematopoietic stem cells and/or hematopoietic progenitor cells according to (12), wherein the blood cell stimulating factor is at least one species selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).
(14) The method of producing hematopoietic stem cells and/or hematopoietic progenitor cells according to (13), wherein the blood cell stimulating factor is at least one species selected from the group consisting of stem cell factor (SCF), thrombopoietin (TPO) and flk2/flt3 ligand (FL).
(15) The method of producing hematopoietic stem cells and/or hematopoietic progenitor cells according to any one of (1) to (14), wherein the hematopoietic stem cells are obtained from the bone marrow, the liver, the spleen, peripheral blood or cord blood.
(16) The method of producing hematopoietic stem cells and/or hematopoietic progenitor cells according to (15), wherein the hematopoietic stem cells are obtained from cord blood.
(17) The method of producing hematopoietic stem cells and/or hematopoietic progenitor cells according to (16), which comprises culturing hematopoietic stem cells and/or hematopoietic progenitor cells in the presence of at least one species selected from the group consisting of stem cell factor (SCF), thrombopoietin (TPO) and flk2/flt3 ligand (FL).
(18) A reagent kit for expanding hematopoietic stem cells and/or hematopoietic progenitor cells, which comprises a compound represented by the above-mentioned formula (I), a tautomer or pharmaceutically acceptable salt of the compound or a solvate thereof as an active ingredient.
(19) A method of producing transformed hematopoietic stem cells, which comprises transferring a gene into hematopoietic stem cells and/or hematopoietic progenitor cells while culturing the hematopoietic stem cells and/or hematopoietic progenitor cells ex vivo in the presence of a compound represented by the formula (I), a tautomer or pharmaceutically acceptable salt of the compound or a solvate thereof, or expanding hematopoietic stem cells carrying a gene transferred into them by culturing the hematopoietic stem cells ex vivo in the presence of a compound represented by the above-mentioned formula (I), a tautomer or pharmaceutically acceptable salt of the compound or a solvate thereof.
(20) The method of producing transformed hematopoietic stem cells according to (19), which uses a culture medium containing at least one blood cell stimulating factor.
(21) The method of producing transformed hematopoietic stem cells according to (20), wherein the blood cell stimulating factor is at least one species selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).
(22) The method of producing transformed hematopoietic stem cells according to any one of (19) to (21), wherein the hematopoietic stem cells and/or hematopoietic progenitor cells are obtained from the bone marrow, the liver, the spleen, peripheral blood or cord blood.
(23) Hematopoietic stem cells and/or hematopoietic progenitor cells obtained by the method as defined in any one of (1) to (17).
(24) Transformed hematopoietic stem cells produced by the method as defined in any one of (19) to (22).
(25) A cell therapy material to be transplanted into a human for treatment of a disease, which comprises hematopoietic stem cells and/or hematopoietic progenitor cells produced by the method as defined in any one of (1) to (17).
(26) A cell therapy material to be transplanted into a human for treatment of a disease, which comprises transformed hematopoietic stem cells produced by the method as defined in any one of (19) to (22).
(27) The cell therapy material according to (25) or (26), wherein the disease to be treated is leukemia, aplastic anemia, lymphopenia, thrombocytopenia, myelodysplastic syndrome, malignant lymphoma, multiple myeloma, myeloproliferative disease, a genetic blood disease, a solid tumor, an autoimmune disease, immunodeficiency, diabetes mellitus, nerve injury, muscle injury, cerebral infarction, myocardial infarction or obstructive arteriosclerosis.
(28) An expanding agent for hematopoietic stem cells and/or hematopoietic progenitor cells, which comprises a compound represented by the above-mentioned formula (I), a tautomer or pharmaceutically acceptable salt of the compound or a solvate thereof.
(29) The expanding agent for hematopoietic stem cells and/or hematopoietic progenitor cells according to (28), wherein the disease to be treated is leukemia, aplastic anemia, lymphopenia, thrombocytopenia, myelodysplastic syndrome, malignant lymphoma, multiple myeloma, myeloproliferative disease, a genetic blood disease, a solid tumor, an autoimmune disease, immunodeficiency, diabetes mellitus, nerve injury, muscle injury, cerebral infarction, myocardial infarction or obstructive arteriosclerosis.

Advantageous Effects of Invention

According to the present invention, it is possible to expand hematopoietic stem cells and/or hematopoietic progenitor cells by culturing hematopoietic stem cells ex vivo by using compounds represented by the above-mentioned chemical formula (hereinafter referred to also as specific compounds). Hematopoietic stem cells and/or hematopoietic progenitor cells produced by using the specific compounds can be used as a cell transplant for treatment of diseases. The specific compounds of the present invention also make it possible to provide a cell transplant (graft) soon as required even from a transplant source which can be obtained in a limited amount, by expanding hematopoietic stem cells and/or hematopoietic progenitor cells easily. Because the specific compounds of the present invention have an effect of expanding hematopoietic stem cells and/or hematopoietic progenitor cells, they are useful as pharmaceutical agents for use in vivo and can be used as preventing, therapeutic or alleviating agent for diseases against which in vivo expansion of hematopoietic stem cells and/or hematopoietic progenitor cells is effective.

The specific compounds of the present invention are low-molecular-weight compounds which can be extracted from plants or produced by ordinary processes for organic synthesis. Therefore, they can be easily extracted or synthesized under conditions under which cells of microorganisms and the like are inviable and can be obtained nearly free of impurities by stricter purification. Therefore, the method using the specific compounds makes it possible to prevent contamination with an unknown pathogen or a biomaterial from an animal other than human, as compared with conventional methods using a protein such as cytokines and growth factors obtained by gene recombination technology. Namely, hematopoietic stem cells produced by the method of the present invention can avoid infection, contamination with foreign genes or immune response to foreign proteins. While being proteins, cytokines and growth factors can be stored or used within very narrow optimal ranges in terms of pH, heat and ion strength, the specific compounds can be used and stored under relatively broad ranges of conditions. In addition, because the specific compounds can be produced inexpensively and continuously unlike proteins, it is possible to eventually reduce treatment cost.

DESCRIPTION OF EMBODIMENTS

Figure 1:
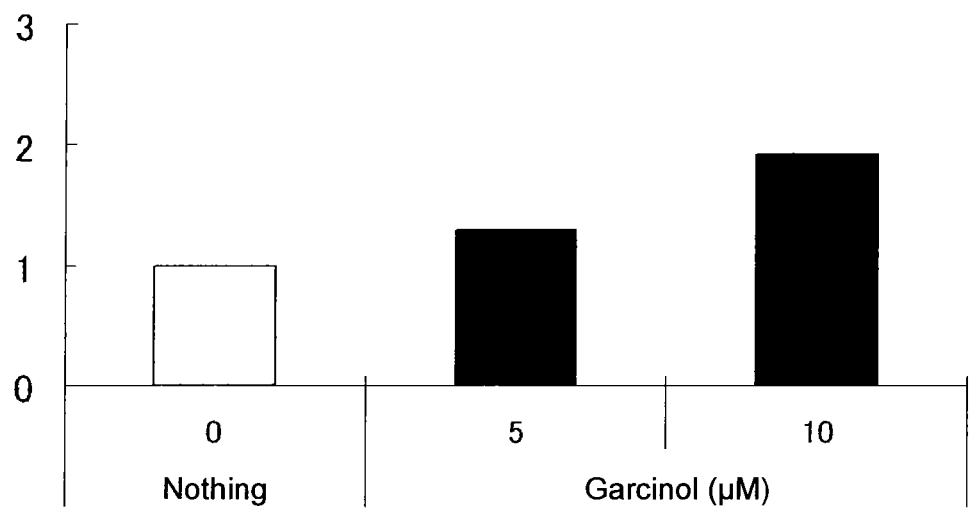
FIG. 1 A graph showing that $CD34^+$ cells were expanded more remarkably in a culture of $CD34^+$ cells in the presence of a specific compound than in the absence of the specific compound. The ordinate of the graph is the number of $CD34^+$ cells cultured in the presence of the specific compound relative to that in the absence of the compound.

Now, the present invention will be described in further detail.

The terms used herein are defined as follows.

Hematopoietic stem cells are defined as cells having both pluripotency which allows them to differentiate into blood cells of all lineages and the ability to regenerate themselves while maintaining the pluripotency.

Multipotent hematopoietic progenitor cells are cells which can differentiate into a plurality of blood cell lineages, though not into all blood cell lineages.

Unipotent hematopoietic progenitor cells are cells which can differentiate into only one blood cell lineage.

Hematopoietic progenitor cells are a group of cells which covers both multipotent and unipotent hematopoietic progenitor cells. For example, the hematopoietic progenitor cells in the present invention may be granulocyte-macrophage colony forming cells (CFU-GM), eosinophil colony forming cells (EO-CFC), erythroid burst forming cells (BFU-E) as erythroid progenitor cells, megakaryocyte colony forming cells (CFU-MEG) or myeloid stem cells (mixed colony forming cells, CFU-GEMM). Among them, cells forming multipotent colonies with diameters of at least 1 mm are called HPP-CFU colony forming cells and are defined as the least differentiated hematopoietic progenitor cells, along with mixed colony forming cells (CFU-GEMM) (McNiece, I. K., et al. 1989. Detection of a human CFC with a high proliferative potential. Blood. 74: 609-612.).

$CD34^+$ means expressing CD (cluster of differentiation) 34 antigen on the cell surface. This antigen is a marker for hematopoietic stem cells and/or hematopoietic progenitor cells and disappears as the cell differentiates. Populations of $CD34^+$ cells are enriched with hematopoietic stem cells and/or hematopoietic progenitor cells. In the present invention, $CD34^+$ cells mean a cell population containing $CD34^+$ cells unless otherwise noted. The same applies to the after-mentioned $CD34^+CD38^-$ cells.

$CD38^-$ means not expressing CD38 antigen on the cell surface. The expression of this antigen increases as blood cells differentiate.

CD34$^+$CD38$^-$ cells mean cells expressing CD34 antigen but not expressing CD38 antigen. CD34$^+$CD38$^-$ cells are characterized as a group of cells containing more hematopoietic stem cells than CD34$^+$ cells.

It has become possible to experimentally test for the presence of human hematopoietic stem cells which have bone marrow repopulating ability by using NOD/SCID mice obtained by crossing diabetic mice and immunodeficient mice. The cells detected by this assay are called SCID-repopulating cells (SRC) and considered the closest to human hematopoietic stem cells.

In the present invention, differentiation of hematopoietic stem cells and/or hematopoietic progenitor cells covers conversion of hematopoietic stem cells to hematopoietic progenitor cells, conversion of multipotent hematopoietic progenitor cells to unipotent hematopoietic progenitor cells and conversion of hematopoietic progenitor cells to cells having specific functions, i.e., mature blood cells such as erythrocytes, leukocytes and megakaryocytes.

In the present invention, expansion of hematopoietic stem cells means that the number of hematopoietic stem cells after culturing is greater than that before culturing. Expansion of hematopoietic progenitor cells means that the number of hematopoietic stem progenitor cells after culturing is greater than that before culturing (which may be 0). Not only the number of hematopoietic stem cells but also the number of hematopoietic progenitor cells in a hematopoietic stem cell culture can be greater after culturing than before culturing as a result of differentiation of some hematopoietic cells into hematopoietic progenitor cells, even with no eventual increase in the number of hematopoietic stem cells in some cases.

In the present invention, the hematopoietic stem cells before culturing may be a cell population containing cells other than hematopoietic stem cells (such as hematopoietic progenitor cells) like the above-mentioned CD34$^+$ cells.

In the present invention, the cell population after culturing may be a cell population containing only hematopoietic stem cells resulting from self-renewal of hematopoietic stem cells in the culture, a cell population containing of hematopoietic progenitor cells differentiated from hematopoietic stem cells or a cell population containing both hematopoietic stem cells and hematopoietic progenitor cells. Usually, cultured cells are a population containing both hematopoietic stem cells and hematopoietic progenitor cells resulting from self-renewal and differentiation of hematopoietic stem cells. When the main purpose is expansion of hematopoietic stem cells, the number of hematopoietic progenitor cells may be greater or smaller after culturing than before culturing.

In the present invention, hematopoietic stem cell expansion activity means the ability to proliferate hematopoietic stem cells having the above-mentioned functions and increase the number of hematopoietic stem cells having the same functions. In the present invention, hematopoietic stem cell differentiating activity means the ability to induce differentiation of hematopoietic stem cells and convert them into hematopoietic progenitor cells having the above-mentioned functions and further into mature blood cells (such as erythrocytes, leukocytes and megakaryocytes).

The specific compounds used in the present invention act on hematopoietic stem cells and/or hematopoietic progenitor cells and shows such an activity that they help hematopoietic stem cells and/or hematopoietic progenitor cells proliferate and survive when they are cultured ex vivo. The compounds are capable of proliferating hematopoietic stem cells and/or hematopoietic progenitor cells with minimal differentiation.

In some cases of treatment by transplantation of hematopoietic stem cells such as peripheral stem cells and cord blood stem cells, hematopoietic stem cells and/or hematopoietic progenitor cells as the transplant cannot be obtained in sufficient numbers to carry out the transplantation or cannot be transplanted with a high success rate. By using the compounds, it is possible to expand collected hematopoietic stem cells ex vivo and obtain hematopoietic stem cells and/or hematopoietic progenitor cells in the amount required to carry out the transplantation even in such cases. Specifically, it is possible to expand hematopoietic stem cells and/or hematopoietic progenitor cells with minimal differentiation by culturing them in a medium containing the compounds and use them for transplantation. It is also possible to expand hematopoietic stem cells and/or hematopoietic progenitor cells more efficiently by further adding various cytokines or growth factors, by coculturing them with stromal cells, or by further adding other low-molecular-weight compounds which act on hematopoietic stem cells and/or hematopoietic progenitor cells.

In the method of the present invention, the collected cells to be cultured for transplantation may be a cell population containing other cells than hematopoietic stem cells such as hematopoietic progenitor cells or may be an isolated population substantially containing hematopoietic stem cells only, such as CD34$^+$ cells, CD34$^+$CD38$^-$ cells, CD90$^+$ cells, CD133$^+$ cells and the like. The cells may contain either or both of hematopoietic stem cells and hematopoietic progenitor cells and further contain other mature blood cells.

The source of the hematopoietic stem cells and/or hematopoietic progenitor cells in the method of the present invention may be any tissue as long as it contains hematopoietic stem cells, and it may preferably be human bone marrow, peripheral blood, peripheral blood containing hematopoietic stem cells mobilized by a cytokine or the like, spleen, liver or cord blood.

The hematopoietic stem cells can be cultured in a culture vessel generally used for animal cell culture such as a Petri dish, a flask, a plastic bag, a Teflon (registered trademark) bag, optionally after preliminary coating with an extracellular matrix or a cell adhesion molecule. The materials for such a coating may be collagens I to XIX, fibronectin, vitronectin, laminins 1 to 12, nitogen, tenascin, thrombospondin, von Willebrand factor, osteoponin, fibrinogen, various types of elastin, various types of proteoglycan, various types of cadherin, desmocolin, desmoglein, various types of integrin, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The hematopoietic stem cells and/or hematopoietic progenitor cells may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82: 378, 1993; Astori G, Bone Marrow Transplant, 35: 1101, 2005).

The nutrient medium to be used for culturing hematopoietic stem cells by using the compounds of the present invention may be a natural medium, a semi-synthetic medium or a synthetic medium in terms of composition, and may be a solid medium, a semisolid medium or a liquid medium in terms of shape, and any nutrient medium used for animal cell culture, especially for hematopoietic stem cell and/or hematopoietic progenitor cell culture, may be used. As such a nutrient medium, Dulbecco's Modified Eagles's Medium (DMEM), Ham's Nutrient Mixture F12, McCoy's 5A medium, Eagles's Minimum Essential Medium (EMEM), αMEM medium (alpha Modified Eagles's Minimum Essential Medium), RPMI1640 medium, Iscove's Modified Dulbecco's Medium (IMDM), StemPro34 (Invitrogen), X-VIVO 10 (Cambrex), X-VIVO 15 (Cambrex), HPGM (Cambrex), StemSpan H3000 (Stemcell Technologies), StemSpan SFEM (Stemcell Technologies), Stemline II (Sigma-Aldrich) or QBSF-60 (Quality Biological) may be mentioned.

Such a medium may contain sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be added in the medium may be fetal calf serum, human serum, horse serum, insulin, transfferin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. The cytokines to be added to the medium may be interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia inhibitory factor (LIF), oncostatin M (OM), erythropoietin (EPO) and thrombopoietin (TPO), but are not limited to those mentioned above.

The growth factors to be added to the medium may be transforming growth factor-β (TGF-β), macrophage inflammatory protein-1α (MIP-1α), epidermal growth factor (EGF), fibroblast growth factor (FGF), nerve growth factor (NGF), hepatocyte growth factor (HGF), protease nexin I, protease nexin II, platelet-derived growth factor (PDGF), cholinergic differentiation factor (CDF), chemokines, Notch ligand (such as Delta 1), Wnt protein, angiopoietin-like protein 2, 3, 5 or 7 (Angpt 2, 3, 5 or 7), insulin-like growth factor (IGF), insulin-like growth factor binding protein (IGFBP) and Pleiotrophin, but are not limited to those mentioned above.

Besides, recombinant cytokines or growth factors having an artificially modified amino acid sequence such as IL-6/soluble IL-6 receptor complex, and Hyper IL-6 (IL-6/soluble IL-6 receptor fusion protein) may also be added.

Among the above-mentioned cytokines and growth factors, preferred are stem cell factor (SCF), interleukin-3 (IL-3), interleukin-6 (IL-6), interleukin-11 (IL-11), flk2/flt3 ligand (FL), granulocyte colony stimulating factor (G-CSF), granulocyte-macrophage colony stimulating factor (GM-CSF), thrombopoietin (TPO), erythropoietin (EPO), Notch ligand (Delta 1), Pleiotrophin and the like, and more preferred are stem cell factor (SCF), flk2/flt3 ligand (FL), thrombopoietin (TPO) and the like. Cytokines and growth factors are usually added to culture at a concentration of 0.1 ng/mL to 1000 ng/mL, preferably from 1 ng/mL to 100 ng/mL.

In addition, at least one chemical substance known to be effective for expansion of hematopoietic stem cells and/or hematopoietic progenitor cells may be added to the medium singly or in combination. Examples of such substances include copper chelators represented by tetraethylenepentamine, histone deacetylase inhibitors represented by trichostatin A, DNA methylase inhibitors represented by 5-aza-2'-deoxycytidine, retinoic acid receptor ligands represented by all-trans retinoic acid, aldehyde dehydrogenase inhibitors represented by dimethylaminobenzaldehyde, glycogen synthase kinase-3 inhibitors represented by 6-bromoindirubin-3'-oxime (6BIO) and prostaglandin E2, but they are not restricted to those mentioned above.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

When a specific compound of the present invention is added to such a medium as mentioned above, it is first dissolved in an appropriate solvent and added to the medium so that the concentration of the compound will be from 100 nM to 10 mM, preferably from 300 nM to 300 μM, more preferably from 1 μM to 100 μM, particularly preferably from 3 μM to 30 μM. Examples of the appropriate solvent include dimethyl sulfoxide (DMSO) and various alcohols, but it is not restricted thereto. The specific compounds may be immobilized on the surface of the substrate or support used for the culture. The specific compounds may be provided or stored in a certain form, for example, in a solid form as a tablet, a pill, a capsule or a granule, in a liquid form as a solution or suspension in an appropriate solvent or solubilizer, or in the form bound to the substrate or support. When they are formulated into such a form, additives such as a preservative like p-hydroxybenzoates, an excipient like lactose, glucose, sucrose and mannitol; a lubricant like magnesium stearate and talc; a binder like polyvinyl alcohol, hydroxypropylcellulose and gelatin, a surfactant like fatty acid esters, a plasticizer like glycerin may be added. The additives are not restricted to those mentioned above and a person skilled in the art can use any additives of choice.

The hematopoietic stem cells are cultured usually at a temperature of from 25 to 39° C., preferably from 33 to 39° C., in the atmosphere having a $CO_2$ concentration of from 4 to 10 vol %, preferably from 4 to 6 vol %, usually for a period of from 3 to 35 days, preferably from 5 to 21 days, more preferably from 7 to 14 days.

When the hematopoietic stem cells are cocultured with stromal cells by the method of the present invention, collected bone marrow cells may be grown directly in culture. Alternatively, it is possible to separate collected bone marrow into stromal cells, hematopoietic stem cells, hematopoietic progenitor cells and other cells, and coculture the hematopoietic stem cells with stromal cells from an individual other than the bone marrow donor. It is also possible to first grow stromal cells only and add and grow hematopoietic stem cells in coculture. When these cells are cocultured, it is possible to use such media and culture conditions as mentioned above.

Hematopoietic stem cells and/or hematopoietic progenitor cells expanded by the method of the present invention can be used as a cell transplant. Because hematopoietic stem cells can differentiate into blood cells of all lineages, they may be transplanted after differentiated into a certain type of blood cells ex vivo. Hematopoietic stem cells and/or hematopoietic progenitor cells expanded by the method of the present invention may be transplanted as they are, or after enrichment using a cell surface antigen as an index, for example, by a magnetic bead method or by a cell sorting method. Such a cell surface antigen molecule may be CD2, CD3, CD4, CD8, CD13, CD14, CD15, CD16, CD19, CD24, CD33, CD34, CD38, CD41, CD45, CD56, CD66, CD90, CD133 or glycophorin A, but is not restricted thereto. The expanded hematopoietic stem cells and/or hematopoietic progenitor cells may be transplanted to its donor or another individual.

Namely, hematopoietic stem cells and/or hematopoietic progenitor cells expanded by the method of the present invention can be used as a graft for hematopoietic stem cell therapy as a substitute for conventional bone marrow or cord blood transplantation. The transplantation of hematopoietic stem cells and hematopoietic progenitor cells expanded by the method of the present invention is carried out in the same manner as conventional bone marrow or cord blood transplantation, except for the cells to be used. Hematopoietic stem cells and/or hematopoietic progenitor cells expanded by the method of the present invention can also be used as a graft to promote regeneration of nerves and muscles damaged by a traumatic injury or a vascular disorder. The graft to may be a composition containing a buffer solution, an antibiotic, a pharmaceutical in addition to hematopoietic stem cells and/or hematopoietic progenitor cells expanded by the method of the present invention.

The hematopoietic stem cell and/or hematopoietic progenitor cell transplant obtained by expansion by the method of the present invention is useful for treatment of not only various types of leukemia but also various diseases. For example, in a case of treatment of a solid cancer patient by chemotherapy or radiotherapy which may cause myelosuppression as a side effect, the patient can recover from hematopoietic damage quickly if the hematopoietic stem cells and/or hematopoietic progenitor cells collected from the bone marrow or peripheral blood of the patient preliminarily to the treatment are expanded ex vivo and returned to the patient after the treatment. Thus, a more intense chemotherapy becomes available with an improved therapeutic effect. It is also possible to alleviate a deficiency in a certain type of blood cells in a patient by differentiating hematopoietic stem cells and/or hematopoietic progenitor cells obtained by the method of the present invention into such a type of blood cells and returning them into the patient. A transplant obtained by the method of the present invention is effective against diseases accompanying decrease in hematopoietic cells and/or hematopoietic insufficiency, diseases accompanying increase in hematopoietic cells, diseases accompanying hematopoietic dysfunction, decrease in immunocytes, increase in immunocytes, diseases accompanying autoimmunity, immune dysfunction, diseases accompanying nerve damage, diseases accompanying muscle damage and ischemic diseases.

As specific examples, chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), C3 deficiency, congenital anemia such as thalassemia, hemolytic anemia due to enzyme deficiency and sicklemia, lysosomal storage disease such as Gaucher's disease and mucopolysaccharidosis, adrenoleukodystrophy, various kinds of cancers and tumors, especially blood cancers such as acute or chronic leukemia, Fanconi syndrome, aplastic anemia, gramulocytopenia, lymphopenia, thrombocytopenia, idiopathic thrombocytopenic purpura, thrombotic thrombocytopenic purpura, Kasabach-Merritt syndrome, malignant lymphoma, Hodgkin's disease, multiple myeloma, chronic hepatopathy, renal failure, massive blood transfusion of bank blood or during operation, hepatitis B, hepatitis C, severe infections, systemic lupus erythematodes, articular rheumatism, xerodermosteosis, systemic sclerosis, polymyositis, dermatomyositis, mixed connective tissue disease, polyarteritis nodosa, Hashimoto's disease, Basedow's disease, myasthenia gravis, insulin dependent diabetes mellitus, autoimmune hemolytic anemia, snake bite, hemolytic uremic syndrome, hypersplenism, bleeding, Bernard-Soulier syndrome, Glanzmann's thrombasthenia, uremia, myelodysplastic syndrome, polycythemia rubra vera, erythremia, essential thrombocythemia, myeloproliferative disease, traumatic spinal cord injury, nerve injury, neurotmesis, skeletal muscle injury, scarring, diabetes mellitus, cerebral infarction, myocardial infarction, obstructive arteriosclerosis and the like may be mentioned.

Hematopoietic stem cells expanded according to the present invention can be used for gene therapy. Gene therapy using hematopoietic stem cells has been difficult because the transfer of a target gene into hematopoietic stem cells at the stationary phase is inefficient, and hematopoietic stem cells differentiate in culture during a gene transfer procedure. However, use of the low-molecular-weight compounds of the present invention in culture makes it possible to expand hematopoietic stem cells while suppressing differentiation of hematopoietic stem cells and improve the gene transfer efficiency considerably. In the gene therapy, a therapeutic gene is transfected into hematopoietic stem cells using the low-molecular-weight compounds of the present invention, and the resulting transfected cells (i.e., transformed hematopoietic stem cells) are transplanted into patients. The therapeutic gene to be transfected is appropriately selected among genes for hormones, cytokines, receptors, enzymes, polypeptides and the like according to the disease (Advance in Pharmacology 40, Academic Press, 1997). Specific examples of the gene include genes for insulin, amylase, proteases, lipases, trypsinogen, chymotrypsinogen, carboxypeptidases, ribonucleases, deoxyribonucleases, phospholipase A2, esterases, $\alpha$1-antitrypsin, blood coagulation factors (VII, VIII, IX and the like), protein C, protein S, antithrombin, UDP glucuronyl transferase, ornithine transcarbanoylase, hemoglobin, NADPH oxidase, glucocerebrosidase, $\alpha$-galactosidase, $\alpha$-glucosidase, $\alpha$-iduronidase, chytochrome P450 enzymes, adenosine deaminase, Bruton kinase, complements C1 to C4, JAK3, common cytokine receptor $\gamma$ chain, Ataxia Telangiectasia Mutated (ATM), Cystic Fibrosis (CF), myocilin, thymic humoral factor, thymopoietin, gastrin, selectins, cholecystokinin, serotinin, substance P, Major Histocompatibility Complex (MHC), multiple drug resistance factor (MDR-1) and the like.

In addition, RNA genes suppressing expression of disease genes are effective as therapeutic genes and can be used in the method of the present invention. For example, antisense RNA, siRNA, shRNA decoy RNA, ribozymes and the like may be mentioned.

For transfer of a therapeutic gene into hematopoietic stem cells, ordinary gene transfer methods for animal cells, such as those using vectors for animal cells such as retrovirus vectors like murine stem cell vector (MSCV) and Moloney murine leukemia virus (MmoLV), adenovirus vectors, adeno-associated virus (AAV) vectors, herpes simplex virus vectors and lentivirus vectors (for vectors for gene therapy, see Verma, I. M., Nature, 389:239, 1997), calcium phosphate coprecipitation, DEAE-dextran transfection, electroporation, a liposome method, lipofection, microinjection or the like may be used. Among them, retrovirus vectors, adeno-associated virus vectors or lentivirus vectors are preferred because their integration into the chromosomal DNA is expected to allow eternal expression of the gene.

For example, an adeno-associated virus (AAV) vector is prepared as follows. First, 293 cells are transfected with a vector plasmid obtained by inserting a therapeutic gene between the ITRs (inverted terminal repeats) at both ends of wild-type adeno-associated virus DNA and a helper plasmid for supplementing virus proteins and subsequently infected with an adenovirus as a helper virus to induce production of virus particles containing AAV vectors. Instead of the adenovirus, a plasmid for expression of an adenovirus gene which functions as a helper may be transfected. Next, hematopoietic stem cells are infected with the virus particles. It is preferred to insert an appropriate promoter, enhancer, insulator or the like upstream of the target gene in the vector DNA to regulate expression of the gene. Introduction of a marker gene such as a drug resistance gene in addition to the therapeutic gene makes it easy to select cells carrying the therapeutic gene. The therapeutic gene may be a sense gene or an antisense gene.

When hematopoietic stem cells are transfected with a therapeutic gene, the cells are cultured by an appropriate method selected from the culture methods mentioned above for expansion of hematopoietic stem cells by the person in charge. The gene transfer efficiency can be evaluated by a standard method in the art. It is possible to transfect a gene into hematopoietic stem cells otherwise, expand the resulting cells (transformed hematopoietic stem cells) by the above-mentioned method of expanding hematopoietic stem cells and use the resulting transformed hematopoietic stem cells for gene therapy.

The transplant for gene therapy may be a composition containing a buffer solution, an antibiotic, a pharmaceutical and the like in addition to transformed hematopoietic stem cells.

The diseases to be treated by gene therapy targeting blood cells include chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), hepatitis B, hepatitis C, congenital anemia such as thalassemia, hemolytic anemia due to enzyme deficiency, Fanconi's anemia and sicklemia, lysosomal storage disease such as Gaucher's disease and mucopolysaccharidosis, adrenoleukodystrophy, various kinds of cancers and tumors.

The specific compounds of the present invention can be used in pharmaceutical agents for preventing, treating or alleviating diseases against which in vivo expansion of hematopoietic stem cells is effective. Pharmaceutical agents containing the compounds of the present invention as an active ingredient may usually be administered as oral medicines such as tablets, capsules, powder, granules, pills and syrup, as rectal medicines, percutaneous medicines or injections. The pharmaceutical agents may be administered as a single therapeutic agent or as a mixture with other therapeutic agents. Though they may be administered as they are, they are usually administered in the form of medical compositions. As other therapeutic agents, active substances selected from the group consisting of colony stimulating factors, cytokines, chemokines, interleukins, cytokine receptor agonists or antagonists, soluble receptors, anti-receptor agonists or antagonist antibodies, small molecules or peptides functioning by the same mechanisms as at least one of those mentioned above may be mixed in a therapeutically effective amount. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents containing the specific compounds of the present invention for administration to human is usually about from 0.1 to 1000 mg/human/day in the case of oral drugs or rectal administration and about from 0.05 mg to 500 mg/human/day in the case of injections into an adult, though it depends on the age and conditions of the patient. The above-mentioned ranges are mere examples, and the dose should be determined from the conditions of the patient.

The present invention is used when the use of compounds which has activity to expand hematopoietic stem cells and/or hematopoietic progenitor cells are expected to alleviate pathological conditions. The diseases as the targets of pharmaceutical agents containing the specific compounds of the present invention include diseases accompanying decrease in hematopoietic stem cells, degenerative diseases and injuries. Specifically, congenital anemia, autoimmune anemia, myelodysplastic syndrome, granulocytopenia, lymphopenia, thrombocytopenia, idiopathic thrombocytopenic purpura, thrombotic thrombocytopenic purpura, Kasabach-Merritt syndrome, decrease in hematopoietic stem cells and/or hematopoietic progenitor cells accompanying various kinds of cancers and tumors, decrease in hematopoietic stem cells and/or hematopoietic progenitor cells accompanying chemotherapy or radiotherapy of cancers, acute radiation syndrome, delayed repopulation of hematopoietic stem cells and/or hematopoietic progenitor cells after bone marrow, cord blood or peripheral blood transplantation, decrease in hematopoietic stem cells and/or hematopoietic progenitor cells accompanying blood transfusion, leukemia, malignant lymphoma, multiple myeloma, myeloproliferative disease, a genetic blood disease, transverse myelitis, multiple sclerosis, demyelination accompanying brain or spinal cord injury, acute brain damage, head injury, spinal cord injury, peripheral nerve injury, ischemic brain injury, hereditary CNS demyelinating disorders, epilepsy, perinatal asphyxia, asphyxia, anoxia, status epilepticus, cerebral stroke, Alzheimer's disease, Parkinson's disease, Huntington's chorea, baldness, amyotrophic lateral sclerosis, cardiovascular diseases, myocardial infarction, cardiac and vascular diseases, liver diseases, gasterointestinal diseases, slight injury, age-related cell injury, age-related tissue injury, lupus, diabetes mellitus, osteoporosis, glucocorticoid-induced osteoporosis, Paget's disease, bone hypermetabolism, periodontal disease, tooth loss, bone fractures, arthritis, articular rheumatism, osteoarthritis, periprosthetic osteolysis, dysostosis, metastatic bone diseases, macular degeneration, dry eye syndrome, cataract, diabetic retinopathy, glaucoma, vitreous diseases, retinal degeneration and the like may be mentioned.

Preferred embodiments of the method of expansion and transfection of hematopoietic stem cells and/or hematopoietic progenitor cells and the method of transplantation of the expanded or transfected hematopoietic stem cells and/or hematopoietic progenitor cells by using the compounds of the present invention will be described below.

First, for expansion of hematopoietic stem cells and/or hematopoietic progenitor cells, cord blood, bone marrow, peripheral blood or the like is collected, and a cell population enriched with hematopoietic stem cells and/or hematopoietic progenitor cells is separated from it. As such a cell population, $CD34^+$ cells, $CD34^+CD38^-$ cells, $CD90^+$ cells, $CD133^+$ cells may be mentioned. For example, $CD34^+$ cells can be separated by density centrifugation combined with magnetic cell sorting (MACS) or flow cytometry (Flow Cytometry). For example, CPD (citrate-phosphate-dextran)-treated blood is fractioned by density centrifugation to separate and collect a mononuclear cell enriched fraction (hereinafter referred to as nucleated cell fraction). As density centrifugation, dextran or Ficoll density centrifugation, Ficoll-paque density gradient centrifugation, Percoll discontinuous density gradient centrifugation or Lymphoprep density gradient centrifugation may be mentioned. Then, magnetic beads coated with an anti-human CD34 monoclonal antibody (Miltenyi Biotec; hereinafter referred to CD34 antibody magnetic beads) and the collected nucleated cell fraction are mixed and incubated at from 2 to 8° C. (for about 30 minutes) to bind $CD34^+$ cells in the nucleated cell fraction to the antibody magnetic beads. The antibody magnetic bead/$CD34^+$ cell complexes are separated and collected by a specialized magnetic cell separator such as autoMACS system (Miltenyi Biotec). The $CD34^+$ cells thus obtained are cultured using a compound of the present invention. The conditions, incubator and medium for culturing $CD34^+$ cells, the species and amount of the compound, the kinds and amounts of additives and the incubation time and temperature may be selected appropriately from those disclosed herein by the person in charge, but are not restricted thereto. $CD34^+$ cells are transfected with a gene which is obtained by cloning a target gene into a vector by a standard method in the art, and incubating the vector and $CD34^+$ cells in the presence of the compound of the present invention. The kinds of the target gene and the vector, the transfection method and the culture method may be selected appropriately from those disclosed herein by the person in charge, but are not restricted thereto.

After culturing, the total cell count is measured by trypan blue assay or the like, while the cell culture is stained with an anti CD34 antibody and an anti CD38 antibody labeled with a fluorescent dye such as FITC (fluorescein isothiocyanate), PE (phycoerythrin) or APC (allophycocyanin), and the proportion of $CD34^+CD38^-$ cells is analyzed by flow cytometry. Thus, it is possible to determine how much hematopoietic stem cells and hematopoietic progenitor cells are expanded in the cell culture. The proportion of the least differentiated cells can be determined by subjecting part of the cell culture to colony assay and counting the resulting HPP-CFC colonies. The transgene can be detected by analyzing DNA or RNA extracted from the cells by southern blotting, northern blotting, RT-PCR (Reverse Transcriptase Polymerase Chain Reaction) or the like. The efficiency of transfer of the target gene is determined by detecting the protein expressed by the transgene by ELISA (Enzyme Linked ImmunoSorvent Assay) or flow cytometry using a specific antibody or by measuring the functional activity of the protein by an enzyme assay.

Expanded or transfected hematopoietic stem cells and/or hematopoietic progenitor cells may be infused by drip, for example, in the case of treatment of leukemia, into patients pretreated with an anticancer drug, total body irradiation or an immunosuppressive drug for eradication of cancer cells or for facilitation of donor cell engraftment. In such cases, the disease to be treated, the pretreatment and the cell transplantation method are selected appropriately by the person in charge. The engraftment of transplanted hematopoietic stem cells and/or hematopoietic progenitor cells in the recipient, the recovery of hematopoiesis, the presence of side effects of the transplantation and the therapeutic effect of the transplantation can be judged by an ordinary assay used in transplantation therapy.

As described above, the present invention makes it possible to expand hematopoietic stem cells and/or hematopoietic progenitor cells and to carry out transplantation therapy and gene therapy safely and easily in a short term by using the expanded cells.

Because hematopoietic stem cells and/or hematopoietic progenitor cells can be expanded efficiently by the method of the present invention, the specific compounds of the present invention can be used as a reagent for research on hematopoietic stem cells and/or hematopoietic progenitor cells. For example, in a study to elucidate the factor regulating differentiation and growth of hematopoietic stem cells by identifying the colony forming cells in a culture of hematopoietic stem cells and analyzing the change in cell surface differentiation markers and gene expression, when hematopoietic stem cells are cultured in the presence of a putative factor, addition of a compound of the present invention makes it possible to expand the hematopoietic stem cells and/or hematopoietic progenitor cells to be analyzed efficiently. The incubation conditions, the incubator and the culture medium, the species and amount of the compound of the present invention, the kinds and amounts of additives and the incubation time and temperature used to elucidate such a factor may be selected appropriately from those disclosed herein by the person in charge. The colony forming cells emerging in the culture can be observed under a microscope normally used in the art, optionally after staining them using an antibody specific for the colony forming cells. The change in gene expression caused by such a putative factor can be detected by analyzing DNA or RNA extracted from the cells by southern blotting, northern blotting, RT-PCR or the like. The cell surface differentiation markers can be detected by ELISA or flow cytometry using a specific antibody to examine the effect of the putative factor on differentiation and growth of the cells.

The specific compounds used in the method of the present invention can be prepared by chemical syntheses, extraction from plants containing the compounds, or chemical modification of substituents in compounds extracted from plants without any particular restrictions.

An example of chemical modifications of extracts from plants is conversion of a hydroxyl group as $R^1$ or $R^2$ in a compound represented by the formula (I) to a $C_{1-3}$ alkoxy group, a $C_{1-3}$ alkylsulfonyl group, a monosaccharide residue, an oligosaccharide residue or an amino acid residue.

Now, the compounds to be used in the present invention will be described in terms of the definitions of terms used for it and its best mode.

In the compounds to be used in the present invention, "n" denotes normal, "i" denotes iso, "t" denotes tertiary, "c" denotes cyclo, "o" denotes ortho, "m" denotes meta, and "p" denotes para.

First, the terms in the respective substituents $R^1$ to $R^6$ and the like will be explained.

A $C_{1-3}$ alkyl group is an alkyl group having from 1 to 3 carbon atoms and may be linear, branched or a $C_3$ cycloalkyl group. As specific examples, a methyl group, an ethyl group, a n-propyl group, an i-propyl group and a c-propyl group and the like may be mentioned.

A $C_{1-10}$ alkyl group is an alkyl group having from 1 to 10 carbon atoms and may be linear, branched or a $C_{3-10}$ cycloalkyl group. As specific examples, in addition to the above-mentioned $C_{1-3}$ alkyl groups, a n-pentyl group, a n-hexyl group, a n-octyl group, a n-decyl group, a t-butyl group, a cyclohexyl group and the like may be mentioned.

A $C_{2-10}$ alkenyl group is an alkenyl group having from 2 to 10 carbon atoms and may be linear, branched or a $C_{3-10}$ cycloalkenyl group. As specific examples, a vinyl group, an allyl group, a hexenyl group, an octenyl group, a decenyl group, a 1,1-dimethylvinyl group, a cyclohexenyl group, a 3-methyl-3-butenyl group, a 3-methyl-2-butenyl group and the like may be mentioned.

A $C_{1-3}$ alkoxy group is an alkoxy group having from 1 to 3 carbon atoms and has such a $C_{1-3}$ alkyl group as mentioned above as the alkyl moiety. As specific examples, a methoxy group, an ethoxy group, a n-propoxy group, an i-propoxy group, a c-propoxy group and the like may be mentioned, and as a preferred example, a methoxy group may be mentioned.

A $C_{1-3}$ alkylsulfonyl group is an alkylsulfonyl group having from 1 to 3 carbon atoms and has such a $C_{1-3}$ alkyl group as mentioned above as the alkyl moiety. As specific examples, a methylsulfonyl group, an ethylsulfonyl group, a n-propylsulfonyl group, an i-propylsulfonyl group, a c-propylsulfonyl group and the like may be mentioned, and as a preferred example, a methylsulfonyl group may be mentioned.

A monosaccharide residue is a saccharide residue having from 1 to 6 carbon atoms. As specific examples of monosaccharides, glycerylaldehyde, erythrose, threose, ribose, lyxose, xylose, arabinose, allose, talose, gulose, glucose, altrose, mannose, galactose, idose, dihydroxyacetone, erythrulose, xylilose, ribulose, psicose, fructose, sorbose, tagatose and the like may be mentioned, and as preferred examples, glucose, mannose and galactose may be mentioned.

An oligosaccharide residue is a sugar residue consisting of from 2 to 6 monosaccharides connected by glucoside linkages, and as specific examples of oligo saccharides, sucrose, lactose, maltose, trehalose, turanose, cellobiose, raffinose, melezitose, maltotriose, acarbose, stachyose, maltopentose, maltohexaose and the like may be mentioned, and as preferred examples, sucrose and lactose may be mentioned.

An amino acid residue is a residue of an a-amino acid having from 2 to 11 carbon atoms, and as specific examples of the amino acid, tryptophan, lysine, methionine, phenylalanine, threonine, valine, isoleucine, leucine, histidine, alanine, arginine, asparagine, serine, aspartic acid, cysteine, glutamine, glutamic acid, glycine, proline, tyrosine and the like may be mentioned, and as preferred examples, glycine and arginine may be mentioned.

When $R^3$ forms a single bond, together with $R^4$, it is meant that the oxygen atom attached to $R^3$ and the carbon atom attached to $R^4$ are bonded by a single bond. When $R^4$ forms a single bond, together with $R^3$, the same is meant.

When $R^4$ forms a single bond, together with $R^5$, it is meant that the single bond connects the carbon atom attached to $R^4$ and the carbon atom attached to $R^5$ so that the carbon atoms are bonded by a double bond. When $R^5$ forms a single bond, together with $R^4$, the same is meant.

Next, preferred examples of each substituent in the formula (I) are given below.

$R^1$ and $R^2$ are preferably $C_{1-3}$ alkoxy group or hydroxyl groups, more preferably hydroxyl groups and may be the same as or different from each other.

The $C_{1-10}$ alkyl group as $R^6$ is preferably a $C_{4-6}$ alkyl group having from 4 to 6 carbon atoms, more preferably a $C_5$ alkyl group having 5 carbon atoms, further preferably a 3-methyl-butyl group.

$R^6$ is preferably a $C_{2-10}$ alkenyl group, and the $C_{2-10}$ alkenyl group as $R^6$ is preferably a linear or branched alkenyl group having from 4 to 6 carbon atoms and one unsaturated bond, more preferably a linear or branched $C_5$ alkenyl group having 5 carbon atoms and one unsaturated bond, further preferably a 3-methyl-3-butenyl group or a 3-methyl-2-butenyl group, particularly preferably a 3-methyl-2-butenyl group.

Favorable compounds as the specific compounds to be used for the present invention are as follows.

(1) Compounds represented by the formula (I) wherein $R^1$ and $R^2$ are hydrogen atoms, $R^3$ is a hydrogen atom, and $R^4$ and $R^5$ form a single bond together with each other.

(2) Garcinol [also called Camboginol] which is such a compound as mentioned above and has a specific steric configuration represented by the following (II).

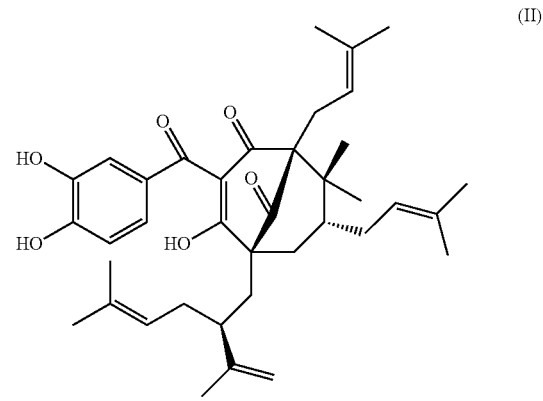

(3) Compounds represented by the formula (I) wherein $R^1$ and $R^2$ are hydrogen atoms, $R^3$ and $R^4$ form a single bond together with each other, and $R^5$ is a hydrogen atom.

(4) Isogarcinol [also called Cambogin], which is such a compound as mentioned above and has a specific steric configuration represented by the following (III).

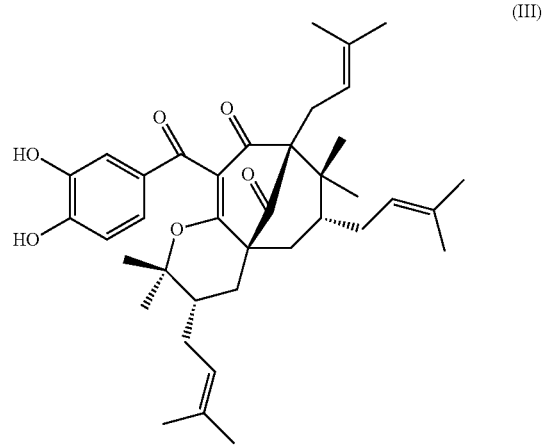

(5) Xathochymol represented by the following formula (IV).

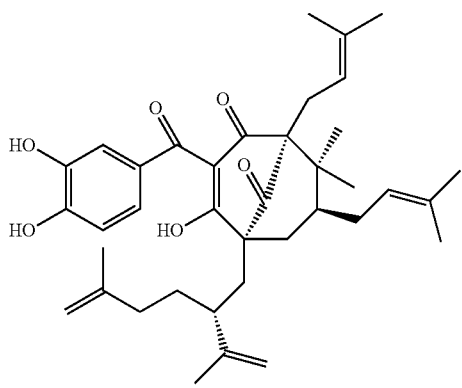

(IV)

(6) Isoxanthochymol represented by the following formula (V).

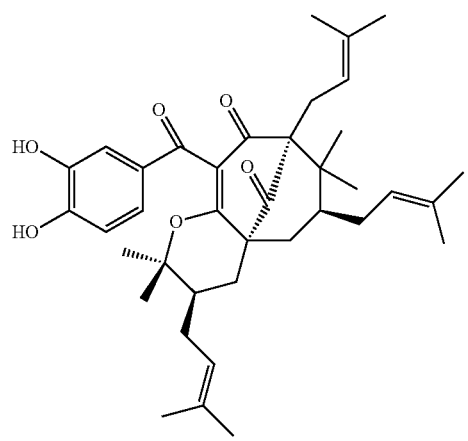

(V)

(7) O-Monomethylisogarcinol represented by the following formula (VI).

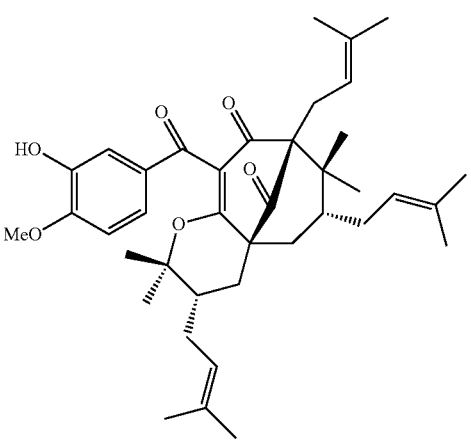

(VI)

Among them, garcinol (see: Krishnamurthy, N. et al. Tetrahedron Lett. 1981; 793) and isogarcinol have especially strong expansion activity on hematopoietic stem cells and are preferred to be used in the present invention.

A specific compound used in the method of the present invention may be in the form of a plant containing it or its pulverization product (whether raw or dried), or a plant extract and/or its partially purified product mentioned later.

The specific compounds used in the present invention are contained in plants of the Guttiferae family such as tropical plants like *Garcinia cambogia* (English name: Goraka), *Garcinia indica* (English name: Kokam), *Garcinia purpurea*, *Garcinia mangostana*, *Garicinia subelliptica* and the like. Any parts of these plants such as fruit, fruit skin, tree, bark or sap may be used. Dry fruit of *Garcinia cambogia* or *Garcinia indica* may be used as it is produced in large amounts as an acidulant in various regions of India. Extraction residues of dry fruit of these plants produced as industrial waste may also be used as in recent years, hydroxycitric acid is industrially extracted from dry fruit of these plants on a large scale.

Although the specific compounds of the present invention are obtainable synthetically, it is preferred to extract them from various plants containing them such as those mentioned above by conventional techniques. These compounds can be extracted efficiently with an organic solvent or a supercritical gas. As the organic solvent, methanol, ethanol, acetone, ethyl acetate, a hydrate thereof, chloroform, dichloromethane, pentane, hexane, heptane and the like may, for example, be mentioned. Among these organic solvents, ethanol, acetone, hexane or the like is preferably used for extraction of the specific compounds of the present invention. For extraction with a supercritical gas, for example, carbon dioxide gas is used as the supercritical gas with an entrainer such as ethanol or water, and a temperature of from 0 to 100° C., preferably from 20 to 40° C., a pressure of from 5 to 2000 kg/cm$^2$, preferably from 20 to 800 kg/cm$^2$, a time of from 5 minutes to 4 days, preferably from 30 minutes to 20 hours and other conditions are appropriately combined. In the present invention, an extract obtained by any of the above-mentioned methods may be used.

A specific compound of the present invention can be obtained by known extraction or purification methods (see: Krishmanurthy, N. et al., Tetrahedron Lett. 22; 793. 1981, Munekazu, I. Et al., Biol. Pharm. Bull. 19; 311. 1996, Delphine R. et al., J. Nat. Prod. 63; 1070. 2000, Chihiro, I. Et al., J. Nat. Prod. 66; 206. 2003). For example, appropriately pulverized fruit, fruit skin, tree, bark or the like of such a plant as mentioned above or sap of the plant is treated with such an organic solvent as mentioned above by a known method. Specifically speaking, an extract containing the compound can be obtained by treatment with from 1 to 100 times (weight ratio), preferably from 3 to 20 times (weight ratio) as much of the organic solvent at a temperature of 0° C. or above, preferably from 10° C. to the boiling point of the organic solvent for from 1 minutes to 8 weeks, preferably from 10 minutes to 1 week. Though the extract itself can be used in the method of the present invention, it is preferred to remove an organic solvent by an ordinary method, for example, by using a rotary evaporator. After removal of an organic solvent, the extract may be treated by ordinary techniques such as freeze drying and heat drying. The compound can be purified by the extract by known methods for separation and purification of natural organic compounds. For example, the compound can be purified by removing impurities by using liquid-liquid extraction, fractional precipitation, crystallization, various types of ion exchange chromatography, gel filtration chromatography using Sephadex LH-20 or the like, adsorption chromatography using activated carbon or silica gel, adsorption/desorption of an active substance or high performance liquid chromatography using a reverse phase column singly, in an appropriate order of combination or repeatedly. Specifically speaking, the extract may be eluted with a 60 to 100% (v/v)

ethanol solution (or an appropriate concentration of methanol or acetonitrile) by ODS-column chromatography into fractions. From collected fractions obtained by chromatographic separation, the compound is obtained upon concentration or crystallization. The compound can be converted further to another derivative, and such a derivative can also be used in the present invention (see: Mantelingu, K. et al., Chemistry & Biology. 14; 645. 2007, JP-A-11-29465).

Specifically speaking, in the case of garcinol or isogarcinol obtained from a plant as described above, its derivative obtained by substituting the hydroxyl group as $R^1$ and/or $R^2$ in the compound represented by the formula (I) with a $C_{1-3}$ alkoxy group, a $C_{1-3}$ alkylsulfonyl group, a monosaccharide residue such as glucose or fructose, an oligosaccharide residue such as sucrose or lactose or an amino acid residue such as glycine or arginine can be used in the present invention, too. A derivative substituted with a $C_{1-3}$ alkoxy group can be obtained by treatment of garcinol or isogarcinol with the corresponding alkyl halide in the presence of a base such as potassium carbonate followed by purification, for example, by silica gel column chromatography. A derivative substituted with a $C_{1-3}$ alkylsulfonyl group can be obtained by an ordinary method, for example, by reacting a solution of garcinol or isogarcinol in pyridine with an alkylsulfonyl chloride. A derivative substituted with a glucose residue can be obtained by an ordinary method, for example, the 14-O-glycopyranosyl derivative having a glucose residue at the 14-position in the formula (I) or the formula (II) can be obtained as desired by reacting a solution of garcinol or isogarcinol in pyridine with 200 mg of 10-bromoacetylglucose for a predetermined time and deacetylating the reaction product in methanol in the presence of potassium carbonate, then concentrating and purifying the reaction mixture by a conventional way, by silica gel column chromatography or the like.

The extract, a partially purified product obtained during the purification step, and the final purified product or a derivative obtained by substituting the final purified product can be used in the present invention alone or in combination of two or more as an active ingredient to be incorporated.

The compounds of the present invention represented by the formula (I) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases or amino acids. They may be salts with inorganic acids (such as hydrochloric acid, hydrobromic acid, phosphoric acid and sulfuric acid) or organic acids (such as acetic acid, citric acid, maleic acid, fumaric acid, benzenesulfonic acid and p-toluenesulfonic acid). The compounds of the present invention represented by the formula (I) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

Garcinol or isogarcinol is ubiquitously present in fruit of plants of the *Garcina* genus. Because the fruit is considered edible, and no reports have been made on the toxicity of the flesh, the compounds are supposed to have no acute toxicity.

EXAMPLES

Now, the present invention will be described in further detail with reference to Examples. However, it should be understood that the present invention is by no means restricted by these specific Examples.

The $CO_2$ concentration in the atmosphere in a $CO_2$ incubator is expressed in vol %. PBS denotes phosphate buffered saline (Sigma-Aldrich Japan), and FBS denotes fetal bovine serum (Hana-Nesco Bio).

MS denotes mass spectrometry, and m/z denotes a mass spectrum.

Reference Synthetic Example 1

Synthesis of Isogarcinol 150 mg (0.249 mmol) of garcinol in toluene (1.2 mL) was stirred with 60 μL of concentrated hydrochloric acid at room temperature for 10 hours. The resulting mixture was allowed to stand in a refrigerator overnight, and the precipitated solid was collected by filtration and rinsed with 6 mL of water. 0.6 mL of acetonitrile was added to the solid to form a slurry, and the slurry was filtered. The slurry obtained from the filtrate was filtered. The collected solids were combined and dried to give 68.7 mg of isogarcinol (yield 46%).

Morphology: white solid

MS m/z: 603$[M+H]^+$

Reference Synthetic Example 2

Synthesis of O-Monomethylisogarcinol

To a solution of isogarcinol 46.0 mg (76 μmol) synthesized in Reference Synthetic Example 1 in acetone (0.8 mL), 158 mg (1.14 mmol) of potassium carbonate and 70 μL (1.1 mmol) of iodomethane were added at room temperature in a nitrogen atmosphere. The mixture was stirred for 40 minutes, and after addition of 20 mL of water, extracted with 80 mL of ethyl acetate, and the extract was washed with 20 mL of saturated aqueous sodium hydrogen carbonate and 20 mL of saturated aqueous sodium chloride, successively, dried over magnesium sulfate, and after filtration, concentrated under reduced pressure. 46.8 mg of the resulting residue was purified by silica gel column chromatography (hexane/ethyl acetate=100/0→85/15 (v/v)) and concentrated under reduced pressure. The resulting viscous substance was dried overnight at 40 to 50° C. to give 17.7 mg of O-monomethylisogarcinol represented by the following formula (VI) (yield 38%).

Morphology: pale yellowish white solid

MS m/z: 617 $[M+H]^+$

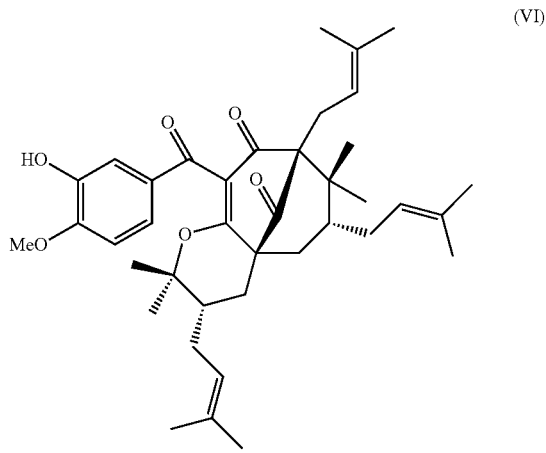

(VI)

Assay Example 1

Expansion of CD34+ Cells and CD34+CD38− Cells Using Human Cord Blood-Derived CD34+ Cells Human cord blood-derived CD34+ cells were purchased from Lonza and plated on a 24-well plate (Corning) (10000 cells/1 mL/well). As the culture medium, StemSpan SFEM (StemCell Technologies) containing 100 ng/mL SCF (Wako Pure Chemical Industries) and 20 ng/mL TPO (PeproTech) in terms of final concentration was used, and garcinol (COSMO BIO) dissolved in dimethyl sulfoxide was added to the medium in an amount of 0.1% (v/v) to a final concentration of 5 or 10 µM. Similarly, isogarcinol (Reference Synthetic Example 1) dissolved in dimethyl sulfoxide was added to the medium in an amount of 0.1% (v/v) to a final concentration of 2 or 5 µM. As a negative control, the medium containing 0.1% (v/v) dimethyl sulfoxide was used.

After the cells were incubated in liquid culture at 37° C. for 7 days in a $CO_2$ incubator (5% $CO_2$), the number of viable cells was counted by trypan blue assay. The number of CD34+CD38− cells was calculated as follows. After the incubation, the cells in the liquid culture was stained with a CD34 antibody (APC, Becton, Dickinson and Company) and a CD38 antibody (P E, Becton, Dickinson and Company), then washed with PBS(−) containing 2% (v/v) FBS and stained with propidium iodide (Sigma-Aldrich Japan) added to a final concentration of 5 µg/mL. The stained cells were analyzed with a BD FACSCANTO™ II flow cytometer (Becton, Dickinson and Company) to determined the proportions of CD34+ cells and CD34+CD38− cells, which was multiplied by the number of viable cells to calculate the numbers of CD34+ cells and CD34+CD38− cells.

Figure 2:
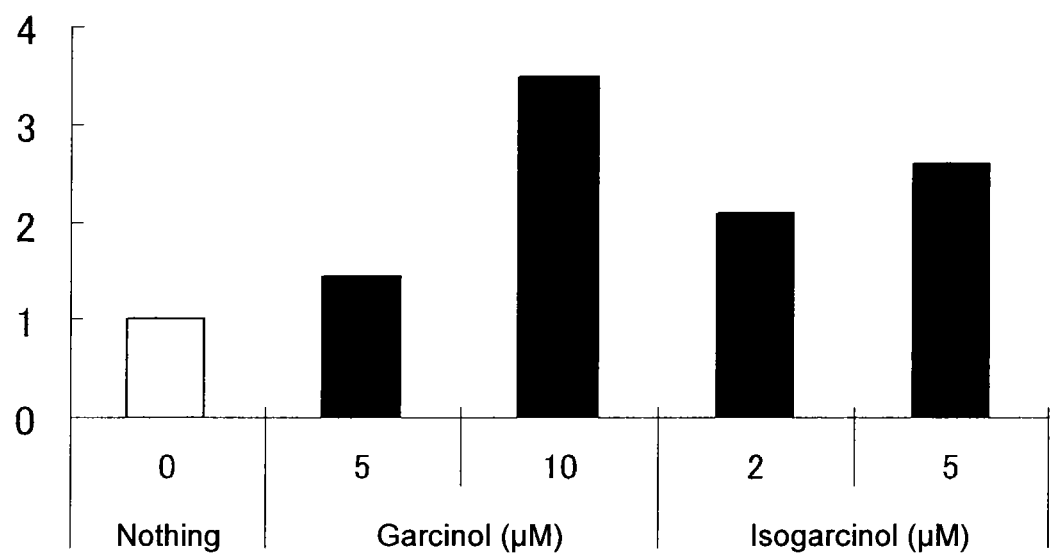
FIG. 2 A graph showing that $CD34^+CD38^-$ cells were expanded more remarkably in a culture of $CD34^+CD38^-$ cells in the presence of a specific compound than in the absence of the specific compound. The ordinate of the graph is the number of $CD34^+CD38^-$ cells cultured in the presence of the specific compound relative to that in the absence of the compound.

The results demonstrate that the compounds of the present invention showed excellent expansion activity on CD34+ cells and CD34+CD38− cells and have expansion activity on hematopoietic stem cells and hematopoietic progenitor cells. The expansion efficiencies in the presence of 5 or 10 µM of garcinol based on the number of CD34+ cells in the absence of compounds are shown in FIG. 1. The expansion efficiencies in the presence of 5 or 10 µM of garcinol or 2 or 5 µM of isogarcinol based on the number of CD34+CD38− cells in the absence of compounds are shown in FIG. 2.

Assay Example 2

Expansion of CD34+CD38− Cells Using Human Cord Blood-Derived CD34+ Cells

Human cord blood-derived CD34+ cells purchased from the same supplier as in Assay Example 1 were plated on a 24-well plate (Corning) (10000 cells/1 mL/well). As the culture medium, StemSpan SFEM (StemCell Technologies) containing 100 ng/mL SCF (Wako Pure Chemical Industries) and 20 ng/mL TPO (PeproTech) in terms of final concentration was used, and O-monomethylisogarcinol (Reference Synthetic Example 2) dissolved in dimethyl sulfoxide was added to the medium to a final concentration of 1 or 2 µM.

After the cells were incubated in liquid culture at 37° C. for 7 days in a $CO_2$ incubator (5% $CO_2$), the number of viable cells was counted by trypan blue assay. The number of CD34+CD38− cells was calculated in the same manner as in Assay Example 1.

Figure 3:
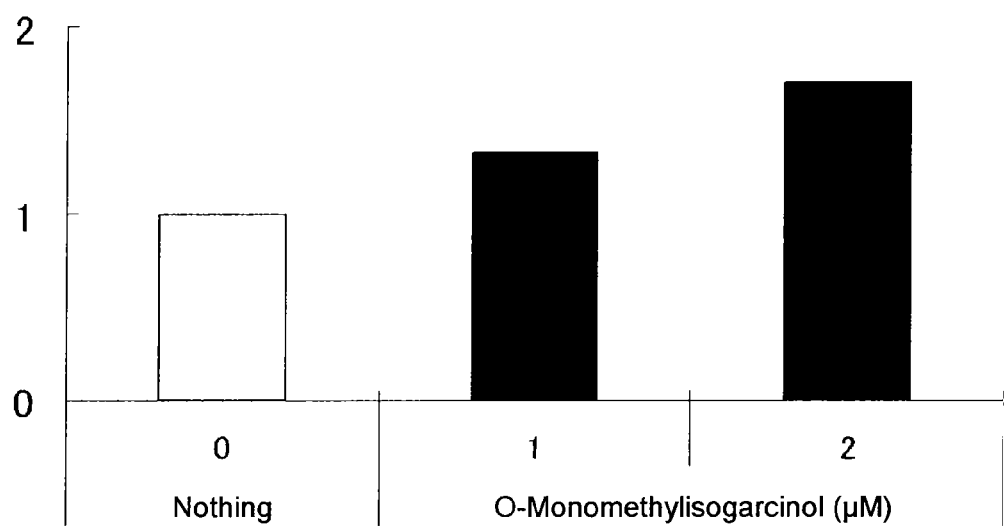
FIG. 3 A graph showing that $CD34^+CD38^-$ cells were expanded more remarkably in a culture of $CD34^+CD38^-$ cells in the presence of a specific compound than in the absence of the specific compound. The ordinate of the graph is the number of $CD34^+CD38^-$ cells cultured in the presence of the specific compound relative to that in the absence of the compound.

The results demonstrate that the compound of the present invention showed excellent expansion activity on CD34+ cells and CD34+CD38− cells and have expansion activity on hematopoietic stem cells and hematopoietic progenitor cells. The expansion efficiencies in the presence of 1 or 2 µM of O-monomethylisogarcinol based on the number of CD34+CD38− cells in the absence of the compound are shown in FIG. 3.

Assay Example 3

Expansion of CD34+CD38− Cells Using Human Cord Blood-Derived CD34+ Cells

Human cord blood-derived CD34+ cells purchased from the same supplier as in Assay Example 1 were plated on a 24-well plate (Corning) (10000 cells/1 mL/well). As the culture medium, StemSpan SFEM (StemCell Technologies) containing 100 ng/mL SCF (Wako Pure Chemical Industries) in terms of final concentration was used, and TPO (PeproTech), Flt-3 ligand (FL, Wako Pure Chemical Industries) and garcinol were added in combinations to final concentrations of 20 ng/mL, 100 ng/mL and 10 µM, respectively.

After the cells were incubated in liquid culture at 37° C. for 7 days in a $CO_2$ incubator (5% $CO_2$), the number of viable cells was counted by trypan blue assay. The number of CD34+CD38− cells was calculated in the same manner as in Assay Example 1.

Figure 4:
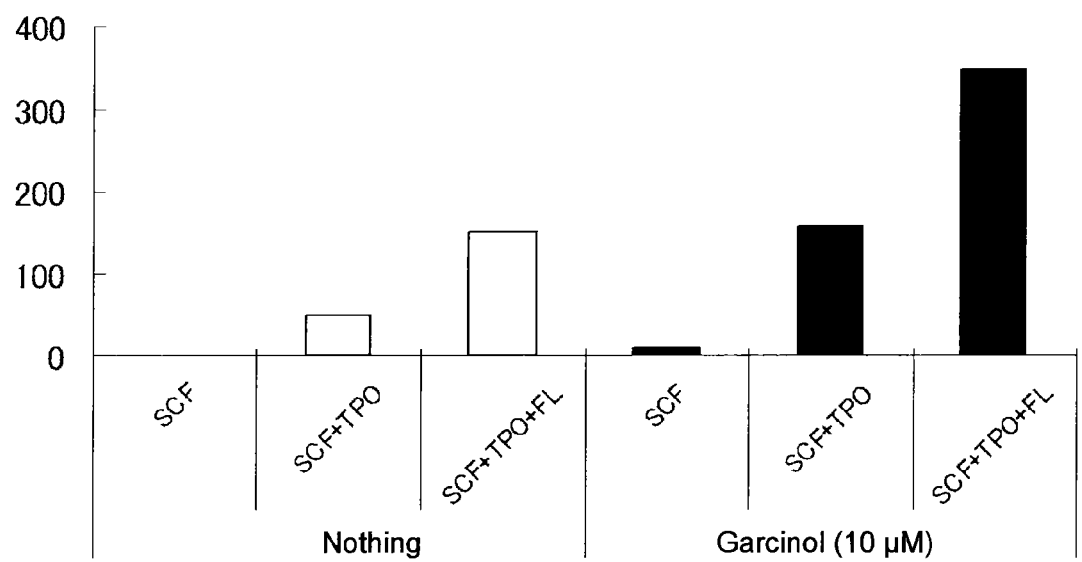
FIG. 4 A graph showing that $CD34^+CD38^-$ cells were expanded more remarkably in a culture of $CD34^+CD38^-$ cells in the presence of a specific compound than in the absence of the specific compound. The ordinate of the graph is the number of $CD34^+CD38^-$ cells cultured in the presence of the specific compound relative to that in the absence of the compound.

The results demonstrate that the compound of the present invention showed higher expansion activity on CD34+CD38− cells in the presence of SCF, in the presence of SCF and TPO or in the presence of SCF, TPO and FL than in the absence of the compound. The expansion efficiencies in the presence of 10 µM of garcinol and various cytokines based on the number of CD34+CD38− cells in the presence of 100 mg/L SCF in terms of final concentration in the absence of the compound are shown in FIG. 4.

Assay Example 4

Expansion of HPP-CFU Using Human Cord Blood-Derived CD34+ Cells

The effects of garcinol and isogarcinol as compounds of the present invention on hematopoietic progenitor cells were measured by blood cell colony forming assay. The liquid cell cultures obtained in Assay Example 1 were poured into 3.5-cm Petri dishes with MethoCult GF H4435 culture medium (StemCell Technologies) at 500 cells/dish and incubated in a $CO_2$ incubator (5% $CO_2$, 37° C.) for 12 days. The number of HPP-CFC colonies in each plate was counted under a microscope routinely. The assay was carried out at least in duplicate, and the numbers of HPP-CFC colonies were averaged.

The results demonstrate that the compounds of the present invention remarkably stimulated formation of HPP-CFU colonies and have expansion activity on hematopoietic progenitor cells.

The results are shown in Table 1.

TABLE 1

| Specific Compound | Number of HPP-CFC colonies |
| --- | --- |
| None | 19 |
| 10 µM garcinol | 35 |
| 5 µM isogarcinol | 42 |

Assay Example 5

Transplantation of Cell Culture into Immunodeficient (NOD/SCID) Mice

Human cord blood-derived CD34+ cells cultured in the presence of 10 µM garcinol (COSMO BIO) in terms of final concentration or in the absence of garcinol (i.e., in a culture medium containing 0.1% (v/v) dimethyl sulfoxide) in the same manner as in Assay Example 1 were transplanted into at least five 7- to 8-week-old NOD/SCID mice by tail vein injection at 4 to 5×10$^4$ cells/mouse in terms of the initial number of CD34$^+$ cells after a sublethal dose of irradiation (2.5 Gy). Eight weeks after the transplantation, the mice were killed, and the bone marrow cells were collected from both thighbones. Subsequently, the bone marrow cells were stained with a human CD45 antibody (APC, Becton, Dickinson and Company), then washed with PBS(−) containing 2%(v/v) FBS and stained with propidium iodide (Sigma-Aldrich Japan) added to a final concentration of 5 μg/mL. The stained cells were analyzed by flow cytometry to determined the proportion of human CD45$^+$ cells in the bone marrow cells. The results demonstrate that the compound of the present invention has an excellent SRC expanding effect and have expansion activity on hematopoietic stem cells.

Figure 5:
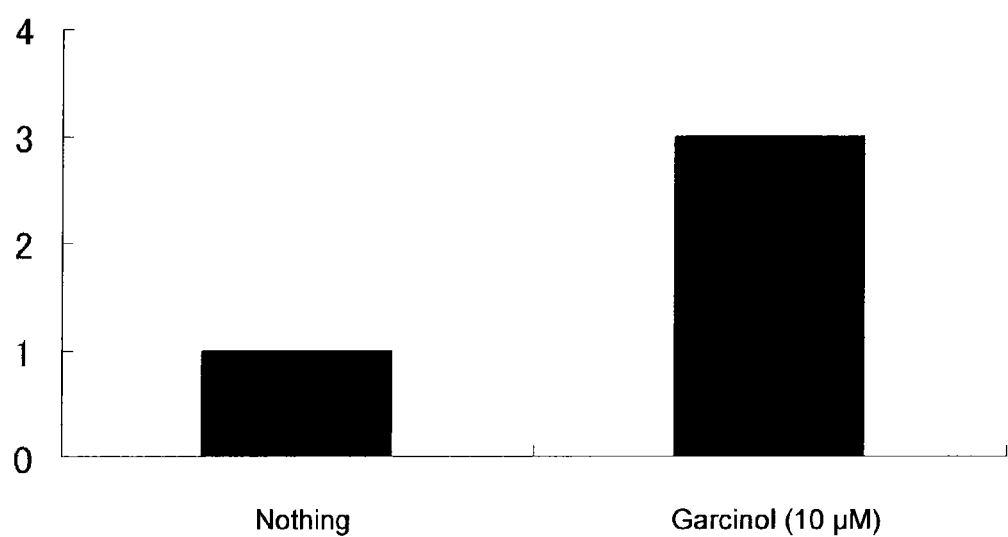
FIG. 5 A graph showing that SRC were expanded more remarkably from $CD34^+$ cells cultured in the presence of a specific compound than from $CD34^+$ cells cultured in the absence of the compound, when assayed after transplantation of the cultured $CD34^+$ cells into immunodeficient mice. The ordinate of the graph is the engrafted proportion of human $CD45^+$ cells in the mice transplanted with the $CD34^+$ cells cultured in the presence of the specific compound based on the proportion of human $CD45^+$ cells in the mice transplanted with those in the absence of the compound.

The engrafted proportion of human CD45$^+$ cells in the mice transplanted with the CD34$^+$ cells cultured in the presence of 10 μM of garcinol based on the proportion of human CD45$^+$ cells in the mice transplanted with those in the absence of garcinol are shown in FIG. 5.

Formulation Example 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| (Total 1000 mg) | |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| (Total 100 mg) | |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (I) | 15 mg |
| Lactose | 90 mg |
| Corn Starch | 42 mg |
| HPC-L | 3 mg |
| (Total 150 mg) | |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| (Total 150 mg) | |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (I) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The specific compounds of the present invention can expand human hematopoietic stem cells and/or hematopoietic progenitor cells in culture ex vivo in a less differentiated state when used as an active ingredient, as compared with in their absence. Cells expanded or transfected by using the compounds of the present invention are useful as a hematopoietic cell transplant for diseases accompanied by hematopoietic dysfunction, ischemia or immune dysfunction and hence application of the cells to cell therapy and gene therapy is expected. The specific compounds of the present invention have effect of expanding human hematopoietic cells and/or hematopoietic progenitor cells, and hence application of the compounds as a drug for a disease accompanied by decrease in hematopoietic stem cells and/or hematopoietic progenitor cells is expected.

The entire disclosures of Japanese Patent Application No. 2010-135431 filed on Jun. 14, 2010 and Japanese Patent Application No. 2010-188594 filed on Aug. 25, 2010 including specifications, claims, drawings and summaries are incorporated herein by reference in their entireties.

The invention claimed is:

1. A method of expanding hematopoietic stem cells and/or hematopoietic progenitor cells, the method comprising:
   culturing hematopoietic stem cells ex vivo in the presence of a compound of formula (I), a tautomer or pharmaceutically acceptable salt of the compound or a solvate thereof:

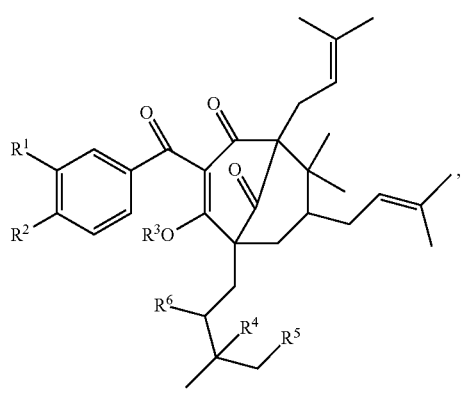

(I)

wherein:
   $R^1$ and $R^2$ are each independently a hydrogen atom, a $C_{1-3}$ alkyl group, a $C_{1-3}$ alkoxy group, a hydroxyl group, a $C_{1-3}$ alkylsulfonyl group, a monosaccharide residue, an oligosaccharide residue, or an amino acid residue;
   $R^3$ is a hydrogen atom or forms a single bond together with $R^4$;
   $R^4$ forms a single bond together with $R^3$ or forms a single bond together with $R^5$;
   $R^5$ is a hydrogen atom or forms a single bond together with $R^4$; and
   $R^6$ is a $C_{1-10}$ alkyl group or a $C_{2-10}$ alkenyl group.

2. The method of claim 1, wherein $R^1$ and $R^2$ are hydroxyl groups.

3. The method of claim 1, wherein $R^6$ is a 3-methyl-2-butenyl group or a 3-methyl-3-butenyl group.

4. The method of claim 1, wherein $R^3$ is a hydrogen atom, and $R^4$ and $R^5$ form a single bond together with each other.

5. The method of claim 4, wherein the compound of formula (I) has formula (II)

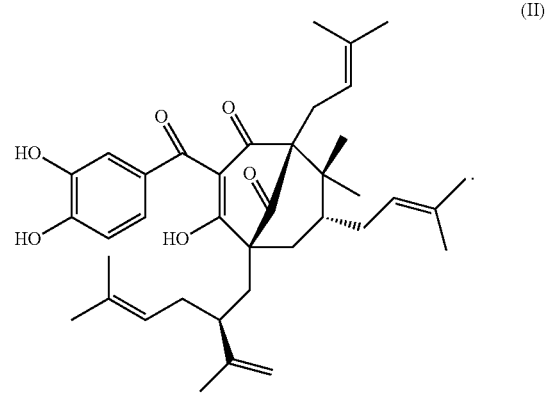

(II)

6. The method of claim 1, wherein $R^3$ and $R^4$ form a single bond together with each other, $R^5$ is a hydrogen atom, and $R^6$ is a 3-methyl-2-butenyl group.

7. The method of claim 6, wherein the compound of formula (I) has formula (III)

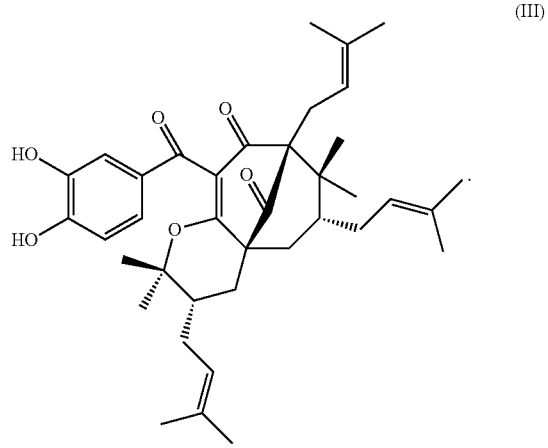

(III)

8. The method of p claim 1, wherein the hematopoietic stem cells and/or hematopoietic progenitor cells to be cultured ex vivo are CD34+ cells.

9. The method of claim 1, wherein the hematopoietic stem cells and/or hematopoietic progenitor cells to be cultured ex vivo are CD34+CD38− cells.

10. The method of claim 1, wherein the cells to be expanded are HPP-CFU colony forming cells.

11. The method of claim 1, wherein the cells to be expanded are SCID-repopulating cells (SRC).

12. The method of claim 1, wherein a culture medium comprising a blood cell stimulating factor is employed.

13. The method of claim 12, wherein the blood cell stimulating factor is at least one species selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO), and erythropoietin (EPO).

14. The method of claim 13, wherein the blood cell stimulating factor is at least one species selected from the group consisting of stem cell factor (SCF), thrombopoietin (TPO), and flk2/flt3 ligand (FL).

15. The method of claim 1, wherein the hematopoietic stem cells are obtained from bone marrow, a liver, a spleen, peripheral blood, or cord blood.

16. The method of claim 15, wherein the hematopoietic stem cells are obtained from cord blood.

17. The method of claim 16, comprising culturing hematopoietic stem cells and/or hematopoietic progenitor cells in the presence of at least one species selected from the group consisting of stem cell factor (SCF), thrombopoietin (TPO), and flk2/flt3 ligand (FL).

* * * * *